(12) United States Patent
Datta

(10) Patent No.: US 9,623,236 B1
(45) Date of Patent: Apr. 18, 2017

(54) LEAD AND CONDUIT PLACEMENT DEVICE AND METHOD

(71) Applicant: Subhajit Datta, Delaware, OH (US)

(72) Inventor: Subhajit Datta, Delaware, OH (US)

( * ) Notice: Subject to any disclaimer, the term of this patent is extended or adjusted under 35 U.S.C. 154(b) by 0 days.

(21) Appl. No.: 15/083,673

(22) Filed: Mar. 29, 2016

Related U.S. Application Data

(62) Division of application No. 14/186,532, filed on Feb. 21, 2014, now Pat. No. 9,370,655.

(60) Provisional application No. 61/774,406, filed on Mar. 7, 2013.

(51) Int. Cl.
*A61B 19/00* (2006.01)
*A61N 1/05* (2006.01)
*A61M 25/06* (2006.01)

(52) U.S. Cl.
CPC ....... *A61N 1/0587* (2013.01); *A61M 25/0662* (2013.01)

(58) Field of Classification Search
CPC ... A61B 19/00; A61B 19/201; A61B 17/3468; A61N 1/05; A61N 1/0587
See application file for complete search history.

(56) References Cited

U.S. PATENT DOCUMENTS

| | | | |
|---|---|---|---|
| 4,146,037 A | 3/1979 | Flynn et al. | |
| 4,271,846 A | 6/1981 | Little | |
| 4,972,847 A | 11/1990 | Dutcher et al. | |
| 5,139,033 A | 8/1992 | Everett et al. | |
| 5,203,772 A | 4/1993 | Hammerslag et al. | |
| 5,342,413 A | 8/1994 | Hirschberg et al. | |
| 5,562,619 A * | 10/1996 | Mirarchi | A61B 17/221 604/264 |
| 5,882,333 A | 3/1999 | Schaer et al. | |
| 5,902,331 A | 5/1999 | Bonner et al. | |
| 5,972,013 A | 10/1999 | Schmidt | |
| 6,120,516 A * | 9/2000 | Selmon | A61B 1/00179 606/159 |
| 6,132,456 A | 10/2000 | Sommer et al. | |
| 6,697,677 B2 | 2/2004 | Dahl et al. | |
| 6,868,291 B1 | 3/2005 | Bonner et al. | |
| 7,270,669 B1 | 9/2007 | Sra | |
| 7,526,342 B2 | 4/2009 | Chin et al. | |
| 7,544,197 B2 | 6/2009 | Kelsch et al. | |
| 7,890,192 B1 | 2/2011 | Kelsch et al. | |
| 7,930,040 B1 | 4/2011 | Kelsch et al. | |
| 2003/0187461 A1 | 10/2003 | Chin | |
| 2004/0153098 A1 | 8/2004 | Chin et al. | |
| 2004/0215139 A1 | 10/2004 | Cohen | |
| 2005/0004644 A1 | 1/2005 | Kelsch et al. | |
| 2006/0009827 A1 | 1/2006 | Kurth et al. | |

(Continued)

FOREIGN PATENT DOCUMENTS

| | | |
|---|---|---|
| WO | WO 99/06104 | 2/1999 |
| WO | WO 2004/058326 | 7/2004 |
| WO | WO 2008/058265 | 5/2008 |

*Primary Examiner* — Victor Nguyen
(74) *Attorney, Agent, or Firm* — Ice Miller LLP

(57) ABSTRACT

The present invention includes devices and methods for lead or conduit placement in tissues or organs. The devices include a lead or conduit placement device that is configured to permit the placement foot, such as a suction foot, to swivel to a desired position with respect to the target tissue, while the lead is releasably attached to the placement foot to permit it to be released from the placement foot after fixing the lead or conduit in the tissue.

18 Claims, 22 Drawing Sheets

(56) References Cited

U.S. PATENT DOCUMENTS

| | | |
|---|---|---|
| 2006/0161238 A1 | 7/2006 | Hall |
| 2009/0182347 A1 | 7/2009 | Ransbury et al. |
| 2009/0198251 A1 | 8/2009 | Ransbury et al. |
| 2010/0312256 A1 | 12/2010 | Kassab et al. |

* cited by examiner

LEAD AND CONDUIT PLACEMENT DEVICE AND METHOD

RELATED APPLICATION DATA

This application is a divisional of U.S. application Ser. No. 14/186,532, filed Feb. 21, 2014, which claims the priority benefit of U.S. Provisional Application No. 61/774,406, filed Mar. 7, 2013, which are hereby incorporated herein in their entirety by reference.

FIELD OF THE INVENTION

The present invention relates to devices and techniques used in thoracoscopic lead placement, and in similar surgical techniques.

BACKGROUND OF THE INVENTION

According to a CDC statistical brief, nearly 5.8 million people in the United States have congestive heart failure. See Lloyd-Jones D, et al. Heart Disease and Stroke Statistics-2010 Update. A Report from The American Heart Association Statistics Committee And Stroke Statistics Subcommittee. Circulation. 2010; 121:E1-E170. About 670,000 people are diagnosed with it each year. Heart failure was a contributing cause of 282,754 deaths in 2006. In 2010, heart failure cost the United States an estimated $39.2 billion. This total includes the cost of health care services, medications, and lost productivity.

Heart failure is a condition in which the heart's pumping power is weaker than normal. With heart failure, blood moves through the heart and body at a slower rate, and pressure in the heart increases. A delay between the contraction of the right and left ventricles often occurs with heart failure, so the walls of the left ventricle are unable to contract synchronously.

Approximately 25-50% of heart failure patients have ventricles that contract asynchronously, and are therefore candidates for biventricular pacing (between 1.5 and 3 million potential patients).

Biventricular pacing, also known as cardiac resynchronization therapy (CRT) utilizes a type of pacemaker that can pace both the septal and lateral walls of the left ventricle.[1] By pacing both the right and left ventricles, the pacemaker can resynchronize a heart.

[1] Pavia S V, Wilkoff B L. Biventricular pacing for heart failure. Cardiol Clin. 2001 November; 19(4):637-51.

Candidates for CRT include patients with severe or moderately severe heart failure symptoms, delayed electrical activation of the heart (such as intraventricular conduction delay or bundle branch block), or those with a history of cardiac arrest or risk factors for cardiac arrest.

CRT improves symptoms of heart failure in about one third of patients who have been treated maximally with medications but still have severe or moderately severe heart failure symptoms. Another third of patients see an improvement in ejection fraction without any major change in symptoms and the last third of the patient population are not responsive to CRT. CRT improves survival, quality of life, heart function, the ability to exercise, and helps decrease hospitalizations in select patients with severe or moderately severe heart failure. CRT can help improve ejection fraction (volume of blood pumped out of the left ventricle) and when combined with an implantable cardiac defibrillator it can help protect against dangerous, fast heart rhythms.[2] Both CRT pacemakers and CRT defibrillators use a left ventricular pacing lead.

[2] Bristow M, et al. Cardiac-resynchronization therapy with or without an implantable defibrillator in advanced chronic heart failure. 2004. N End J Med 350 (21): 2140-50.

The CRT device and its leads can be implanted using an endocardial (transvenous) or epicardial (surgical) approach. The endocardial approach is the most common method. A local anesthetic is given to numb the area. The leads are inserted through an incision in the chest and into a vein. Two leads are guided to the right atrium and right ventricle of the heart, while the third lead is guided through the coronary sinus (the venous system of the heart) to the left ventricle. The lead tips are attached to the heart muscle, while the other ends of the leads are attached to the pacemaker placed in a pocket created under the skin in the upper chest. When the endocardial approach is used, the hospital recovery time is generally 24 hours. The endocardial technique is technically challenging. In some cases, this technique may not be successful due to the size, shape or location of the vein(s). If the endocardial approach cannot be used or is unsuccessful, the epicardial approach is then attempted.

The epicardial approach is a less common method in adults, but more common in children. The leads are placed under general anesthesia and guided to the heart with the aid of the fluoroscopy machine. The locations of lead placement are identical to the endocardial approach. The pulse generator is placed in a pocket created under the skin in the abdomen. Although recovery with the epicardial approach is longer than that of the transvenous approach (generally about 3 to 5 days), minimally invasive techniques have enabled shorter hospital stays and recovery times.

There are several complications and costs associated with conventional pacing that may occur during biventricular pacing, including: (a) localized/skin infection, (b) systemic infection secondary to infected pacing box or lead, (c) bleeding, (d) hematoma, (e) lead displacement, (f) equipment failure, i.e. fractured pacing wire, faulty pacing box and (g) pneumothorax.

Standard predictors of operative complications apply, those being degree of heart failure, the surgical environment, diabetes and the duration of the procedure. Although with experience the procedure times reduce, even in the best hands implantation of the left ventricular lead may be time consuming, contributing to an increased infection risk.[3]

[3] Alonso, C, et al. Six year experience of transvenous left ventricular lead implantation for permanent biventricular pacing in patients with advanced heart failure: technical aspects. Heart. 2001; 86(4):405-410.

In the initial studies of biventricular pacing, the right atrial and right ventricular leads were inserted via the standard transvenous approach, but the epicardial left ventricular lead was placed surgically via thoracotomy or thoracoscopically. These approaches required a larger incision and general anaesthetic, consequently carrying a significant morbidity and mortality.

In 1998, the preferred method of left ventricular lead insertion using the transvenous approach was introduced.[4] The precise location of the lead is ideally the mid left ventricular cavity in a lateral or posterolateral vein.[5] The use of guiding catheters within the coronary sinus and the use of purpose-designed leads have increased success rates and ability to reach the target vessel. Some of these procedures may require the use of multiple types of catheters and guidewires, adding cost to this procedure. The requirement to position a lead in a branch of the coronary sinus and the techniques required to achieve this account for the additional complications and significant failure rate seen with biventricular pacing. Trans-cardiac-venous placement of left ventricular lead occasionally will cause disturbing phrenic nerve stimulation, causing uncomfortable diagphragmatic twitching and necessitate relocation to suboptimal sites. Thoracoscopic placement visualizes the phrenic nerve and thus placement away from nerve can be accomplished at the outset

[4] Daubert, J C, et al. Permanent left ventricular pacing with transvenous leads inserted into the coronary veins. Pacing clin. Electrophysiol. 1998; 21(1 pt 2):239-245.

[5] Auricchio, A, et al. The pacing therapies for congestive heart failure (path-chf) study: rationale, design, and endpoints of a prospective randomized multicenter study. Am. J. Cardiol. 1999; 83(5b):130d-135d.

Although devices of various types have been developed for the endocardial approach, there remains a need for a device that is relatively simple to construct and use, that permits firm and accurate lead or conduit placement in tissue, including cardiac tissue. There also are applications relating to a variety of operations and procedures involving the placement of a variety of leads or conduits in a variety of tissues that likewise would benefit from the device and methods of the present invention.

SUMMARY OF THE INVENTION

The present invention includes devices and methods that may be summarized as follows:

The present invention generally includes a lead or conduit placement device that is configured to permit the placement foot, such as a suction foot, to swivel to a desired position with respect to the target tissue, while the lead is releasably attached to the placement foot to permit it to be released from the placement foot after fixing the lead or conduit in the tissue.

Another aspect of the present invention is to arrange and configure the placement foot and lead (or lead-placing head portion) to be releasably attached. The attachment should be sufficiently firm to allow the lead guide to transmit movement of the lead guide to the placement foot, so as to participate in the articulation of the placement foot in one direction, while being releasable through hand force to permit the lead to be separated from the placement foot after fixing the lead or conduit in the tissue.

The lead placement device of the present invention typically features a suction foot provided with a vacuum through a lumen extending through the device. The device also preferably includes an actuator that transmits movement of the lead guide to the placement foot in a second direction, so as to participate in the articulation of the placement foot. The actuator in the preferred embodiment may extend though the lumen. As an alternative, the actuator may reside outside the lumen.

There are several optional and preferred arrangements of the present invention that are described in its many embodiments.

One variation of the present invention is a lead placement device with a suction foot and releasable lead, optional releasable lead head, with an actuator.

This embodiment of the present invention includes a device adapted for the thoracoscopic placement of a lead at a target site on an epicardial surface of a heart (that being its principal, but non-exclusive mode of use), the device comprising: (a) a hollow lead guide having a lead guide distal end, and connected to a lead guide head at the lead guide distal end; (b) a lead extending through the hollow lead guide and having a lead distal end portion, the lead distal end portion extending from the lead guide head for contact with the epicardial surface of the heart, and releasably engaging the lead guide head; (c) an elongated body having a longitudinal axis, a proximal end portion and a distal end portion, and having a proximal inlet and a distal lead outlet for extending the lead guide head therethrough for contacting the lead with the epicardial surface of the heart, the elongated body comprising (1) a lead receiving passageway for receiving and conducting the lead guide head extending between the proximal inlet and the distal lead outlet therethrough, and (2) a lumen adapted to provide suction to the distal end portion; (d) a suction foot portion in fluid communication with the lumen, the suction foot portion tiltably attached to the distal end portion such that the suction foot may be tilted about two axes with respect to the longitudinal axis (the lead guide head being adapted to releasably engage the suction foot portion such that such engagement is of sufficient strength to maintain the position of the lead distal end portion as it engages the epicardial surface of a heart, and sufficiently releasable such that the lead guide head may be released from the suction foot portion once the lead is attached to the epicardial surface of a heart); and (e) an actuator extending from the proximal end portion to the distal end portion and adapted to tilt the suction foot portion about a first of the axes.

The elongated body may be of any length, but typically will have a lead receiving passageway that has a length in the range of 10 cm to 40 cm for manual devices.

It is preferred that the elongated body be provided with a handle portion extending laterally therefrom for ease of manual use, though it will be appreciated that the invention may be adapted for robotic use.

Another preferred variant of the present invention is a lead placement device with a suction foot and releasable lead, optional releasable lead head, with an actuator that permits the suction foot and releasable lead, with optional releasable lead head, to be swiveled about a second axis.

In this variation, the hollow lead guide additionally and preferably comprises a flexible member connecting the lead guide head to the lead guide distal end, and this flexible member may be any part of sufficient flexibility and resilience to permit the lead guide head and the suction foot to swivel as described herein. For instance the flexible member may be in the form of a metal or plastic spring, or equivalent metal or plastic structure.

It is also preferred that the device be provided with a knob so as to permit the hollow lead guide to be rotated within the elongated body by hand, so as to rotate the lead guide head, to permit the user to twist the metal lead into place, especially where the distal end of the lead wire is in a corkscrew shape as is common.

In a most preferred embodiment the flexible member is of sufficient stiffness in the longitudinal direction (such as with a metal spring), that, upon movement of the hollow lead guide within the elongated body, the suction foot portion may be tilted about a second axis. In this most preferred embodiment the suction foot portion has an engagement aperture aligned with the hollow lead guide, and wherein the lead guide head is adapted to releasably engage the engagement aperture. This releasable engagement may be accomplished by any means acceptable to the device's use, such as through the use of light magnetic forces or adhesives, as well as through the use of mechanical arrangements involving light interferences fits, that are both of sufficient strength to permit the suction foot to be swiveled into the desired position, while allowing the suction foot and the balance of the device to be pulled free after final lead placement.

This permits the lead guide to function both to assist in swiveling the suction foot, and the lead it holds, into position on the heart or other tissue surface, while also holding the lead in position for optional lead testing and ultimate lead placement, followed by release of the suction foot (along with the balance of the device), following final lead placement. In this same preferred embodiment, the suction foot portion defines an engagement aperture aligned with the hollow lead guide, and wherein the lead guide head is adapted to releasably engage the engagement aperture.

Also in the most preferred embodiment described herein, the suction foot portion may be of any shape, such as presenting a round, polygonal, star or ovoid foot print, though it is preferred that it have an arcuate footprint shape and comprise a plurality of air channels in fluid contact with the lumen, so as to be capable of providing suction to the suction foot portion. This shape permits the lead to be more easily separated from the suction foot, and the balance of the device, after final lead placement.

It will be appreciated that the lead itself may be incorporated into supplementary structure for ancillary purposes such as electrical insulation and to be able to mechanically cooperate with the balance of the device and consistent with its function as described herein (such as by providing sleeves and flanges, etc.) One such arrangement involves having the lead distal end be held by a lead guide head (typically of a polymeric material) so as to extend from the distal side of the lead guide head.

The device may also additionally comprise an interferant release collar attached to the lead distal end portion and disposed on the distal side of the suction foot portion, the interferant release collar being larger than the aperture. This allows more precise and oriented lead placement and to prevent accidental or premature retraction of the lead guide head, as described herein.

The actuator of the preferred embodiment of the present invention comprises a flexible member connecting the suction foot portion to the elongated body. This flexible member may be any part of sufficient flexibility and resilience to permit the suction foot to swivel as described herein. For instance the flexible member may be in the form of a metal or plastic spring, or equivalent metal or plastic structure.

In the preferred embodiment the actuator is in turn attached to a knob portion disposed on the proximal end portion, the knob adapted to move the actuator within the elongated body so as to tilt the suction foot about a first of the axes. The actuator may be any part of sufficient flexibility and resilience to facilitate the movement of the suction foot to swivel as described herein. For instance, it is preferred that the actuator comprise a wire attached to a knob portion disposed on the proximal end portion, the knob adapted to move the actuator within the elongated body so as to tilt the suction foot about a first of the axes.

With respect to the lumen and vacuum source for use in the invention in its many embodiments, the device may additionally comprise a source of vacuum suction in fluid communication with the lumen. The source of vacuum suction in fluid communication with the lumen may be any source sufficient for operation of the device, and typically may be selected from the group consisting of a hand pump, or a syringe attached to the elongated body, or a motorized pump supplying vacuum suction to the lumen. The device of the present invention may optionally include a plurality of lumens extending between the proximal inlet and the distal outlet.

The device of the present invention may also include a supplementary test lead extending from the lead guide head and through the elongated body.

Another aspect of the present invention is a lead placement device with a swiveling suction foot as represented, for instance, by the preferred embodiments described herein. It will be appreciated that this aspect of the invention may be constructed and used in other devices beyond that described in the preferred embodiment herein.

This aspect of the present invention may be described as a device adapted for the thoracoscopic placement of a lead at a target site on an epicardial surface of a heart (though it may also be used with other tissues and other purposes, such as biopsy, stent or tubule placement, etc.). The device comprises in general terms, (a) a hollow lead guide; (b) a lead extending through the hollow lead guide, the lead having a lead distal end portion; (c) an elongated body having a longitudinal axis, a proximal end portion and a distal end portion, and having a proximal inlet and a distal lead outlet, the elongated body comprising (1) a lead receiving passageway for receiving and conducting the lead distal end to the distal lead outlet, and (2) a lumen adapted to provide suction to the distal end portion; (d) a suction foot portion releasably attached to the lead distal end portion, and being in fluid communication with the lumen, the suction foot portion swivelably attached to the distal end portion such that the suction foot may be swiveled with respect to the longitudinal axis (the lead adapted to releasably engage the suction foot portion such that such engagement is of sufficient strength to maintain the position of the lead distal end portion as it engages the epicardial surface of a heart, and sufficiently releasable such that the lead may be released from the suction foot portion once the lead is attached to the epicardial surface of a heart); and (e) an actuator extending from the proximal end portion to the distal end portion and adapted to tilt the suction foot portion about a first axis with respect to the longitudinal axis, such that the hollow lead guide is adapted to tilt the suction foot portion about a second axis with respect to the longitudinal axis.

Still another aspect of the present invention is a lead placement device with suction foot and releasable lead head and lead with single actuator, wherein the device may be adapted for use with any tissue type and for the placement of any conduit type (such as conduit of electrical current or signals, or gas or liquid fluids conduits) for any medical or veterinary purpose.

This device may be understood as being adapted for the placement of a conduit at a target site on a tissue surface, the device comprising: (a) a hollow conduit guide having a conduit guide distal end, and connected to a conduit guide head at the conduit guide distal end; (b) a conduit extending through the hollow conduit guide and having a conduit distal end portion, the conduit distal end portion extending from the conduit guide head for contact with the tissue surface, and releasably engaging the conduit guide head; (c) an elongated body having a longitudinal axis, a proximal end portion and a distal end portion, and having a proximal inlet and a distal conduit outlet for extending the conduit guide head therethrough for contacting the conduit with the tissue surface, the elongated body comprising (1) a conduit receiving passageway for receiving and conducting the conduit guide head extending between the proximal inlet and the distal conduit outlet therethrough, and (2) a lumen adapted to provide suction to the distal end portion; (d) a suction foot portion in fluid communication with the lumen, the suction foot portion tiltably attached to the distal end portion such that the suction foot may be tilted about two axes with respect to the longitudinal axis (the conduit guide head adapted to releasably engage the suction foot portion such that such engagement is of sufficient strength to maintain the position of the conduit distal end portion as it engages the tissue surface, and sufficiently releasable such that the conduit guide head may be released from the suction foot portion once the conduit is attached to the tissue surface); and (e) an actuator extending from the proximal end portion to the distal end portion and adapted to tilt the suction foot portion about a first of the axes.

The conduit may be selected from the group consisting of liquid and gas conduits, such as conductive materials such as wires or fluid-conductive tubules, such conduits adapted to be placed into tissues for electrical or fluid assay, electrical or fluid testing, electrical actuation, or otherwise to bring about electrical or fluid influence or to determine the level of same. Preferably such conduits will include coiled plastic or metal tubules.

This device may be provided with a handle portion extending laterally from the elongated body for manual operation, but otherwise may be adapted for robotic use in association with a robotic arm to which it may be readily adapted.

As in other variants of the invention, this variant may have a flexible attachment of the hollow lead guide to a lead guide head to permit lead insertion action and suction foot swivel about a second axis, such as described herein.

This variant of the invention may also be used with the hollow conduit guide additionally comprising a flexible member connecting the conduit guide head to the conduit guide distal end.

The flexible member in this embodiment, and its nature and operation, may be the same or equivalent to that described above with respect to other embodiments described above. Likewise, the actuator portion, and its nature and operation may be the same or equivalent to that described above with respect to other embodiments described above.

The source of vacuum suction and its cooperation variants with respect to the fluid communication with the lumen similarly may be the same or equivalent to that described above with respect to other embodiments described above.

It will be appreciated that in another variation of the invention, that a flexible and resilient conduit portion may extend from the distal end of the hollow conduit guide and thereby also serve as a flexible attachment permitting the suction foot to be swiveled while still being of sufficient strength to steer the foot, such that a separate flexible member, such as a spring (as used in the other embodiments describe herein involving a flexible lead), can be eliminated.

In still another variation of the preset invention, there is provided a conduit placement device with swiveling suction foot and releasable lead. This device may be adapted for the placement of a conduit at a target site on a tissue surface, the device comprising: (a) a hollow conduit guide; (b) a conduit extending through the hollow conduit guide, the conduit having a conduit distal end portion; (c) an elongated body having a longitudinal axis, a proximal end portion and a distal end portion, and having a proximal inlet and a distal conduit outlet, the elongated body comprising (1) a conduit receiving passageway for receiving and conducting the conduit distal end to the distal conduit outlet, and (2) a lumen adapted to provide suction to the distal end portion; (d) a suction foot portion releasably attached to the conduit distal end portion, and being in fluid communication with the lumen, the suction foot portion swivelably attached to the distal end portion such that the suction foot may be swiveled with respect to the longitudinal axis (the conduit guide head adapted to releasably engage the suction foot portion such that such engagement is of sufficient strength to maintain the position of the conduit distal end portion as it engages the tissue surface, and sufficiently releasable such that the conduit guide head may be released from the suction foot portion once the conduit is attached to the tissue surface); and (e) an actuator extending from the proximal end portion to the distal end portion and adapted to tilt the suction foot portion about a first axis with respect to the longitudinal axis; wherein the hollow conduit guide is adapted to tilt the suction foot portion about a second axis with respect to the longitudinal axis. This device may be used for the placement of conduits selected from the group consisting of liquid and gas conduits as described herein.

The present invention also includes several optional variants including the use of a flexible tip incorporated into the body of the elongated body, such that the device may be adapted for the thoracoscopic placement of a lead at a target site on an epicardial surface of a heart (or the placement of any other conduit into any other type of tissue as described herein) This variant of the device comprises: (a) a hollow lead guide having a lead guide distal end, and connected to a lead guide head at the lead guide distal end; (b) a lead extending through the hollow lead guide and having a lead distal end portion, the lead distal end portion extending from the lead guide head for contact with the epicardial surface of the heart, and releasably engaging the lead guide head; (c) an elongated body having a longitudinal axis, a proximal end portion and a flexible distal end portion, and having a proximal inlet and a distal lead outlet for extending the lead guide head therethrough for contacting the lead with the epicardial surface of the heart, the elongated body comprising (1) a lead receiving passageway for receiving and conducting the lead guide head extending between the proximal inlet and the distal lead outlet therethrough, and (2) a lumen adapted to provide suction to the distal end portion; (d) a suction foot portion in fluid communication with the lumen, the suction foot portion attached to the flexible distal end portion such that the flexible distal end portion may be swiveled with respect to the longitudinal axis; the lead guide head adapted to releasably engage the suction foot portion such that such engagement is sufficient to (1) maintain the position of the lead as it engages the epicardial surface of a heart, and sufficiently releasable such that the lead guide head may be released from the suction foot portion once the lead is attached to the epicardial surface of a heart; and (e) at least one actuator extending from the proximal end portion and adapted to swivel the flexible distal end portion with respect to the longitudinal axis. The device of the present invention may comprise two actuators extending from the proximal end portion and adapted to swivel the flexible distal end portion in respective two directions with respect to the longitudinal axis.

The flexible distal end portion may include a hinge or may be constructed of a corrugated tube to permit flexion and swiveling motion.

Other aspects of the device of the present invention and which may be used with the foregoing embodiments include the following:

The device of the present invention may include a suction foot portion that is collapsible and is adapted to be reversibly moved from a stored position within the elongated body to a deployed position outside the elongated body. The collapsible suction foot portion may comprise an array of collapsible fronds adapted to form into a point when in the stored position.

The device of the present invention may include, on the elongated body, a closure lid adapted to reversibly open and close the distal lead outlet.

The device of the present invention may include a telescoping portion of the elongated body, so as to be deflectable by the actuator(s).

In still another embodiment of the present invention, the devices as described herein may additionally comprise a supplementary suction foot portion positioned so as to be capable of retracting tissue, the supplementary suction foot portion additionally comprising cutting means adapted to cut tissue, and being positioned and defining a passageway such that the suction foot portion may pass therethrough.

Such a device may have a supplementary suction foot portion that is adapted and configured for pericardiac retraction. In this embodiment, the supplementary suction foot portion may comprise two concentrically arranged suction pads, and wherein the cutting means comprises an electrocautery blade disposed between the concentrically arranged suction pads.

Some of the foregoing additional embodiments and variants of the present invention are described and depicted in Appendix A hereto.

The present invention also includes several methods related to lead and/or conduit placement, which may be carried out with devices in accordance with the present invention or other devices adapted for the same purpose. The present invention also includes several methods that may be described by the steps inherent in the use of any of the devices of the present invention, as described herein.

The present invention includes a method for the thoracoscopic placement of a lead at a target site on an epicardial surface of a heart of a non-human animal, the method comprising: (a) extending into the pericardial region a device comprising: a hollow lead guide having a lead guide distal end, and connected to a lead guide head at the lead guide distal end; a lead extending through the hollow lead guide and having a lead distal end portion, the lead distal end portion extending from the lead guide head for contact with the epicardial surface of the heart, and releasably engaging the lead guide head; an elongated body having a longitudinal axis, a proximal end portion and a distal end portion, and having a proximal inlet and a distal lead outlet for extending the lead guide head therethrough for contacting the lead with the epicardial surface of the heart, the elongated body comprising (1) a lead receiving passageway for receiving and conducting the lead guide head extending between the proximal inlet and the distal lead outlet therethrough, and (2) a lumen adapted to provide suction to the distal end portion; a suction foot portion in fluid communication with the lumen, the suction foot portion tiltably attached to the distal end portion such that the suction foot may be tilted about two axes with respect to the longitudinal axis; the lead guide head adapted to releasably engage the suction foot portion such that such engagement is of sufficient strength to maintain the position of the lead as it engages the epicardial surface of a heart, and sufficiently releasable such that the lead guide head may be released from the suction foot portion once the lead is attached to the epicardial surface of a heart; and an actuator extending from the proximal end portion and adapted to tilt the suction foot portion about a first of the axes; (b) positioning the suction foot portion upon the epicardial surface; (c) applying suction through the lumen so as to stabilize the suction foot against the epicardial surface; (d) inserting the lead distal end portion into the epicardial surface; (e) disengaging the lead guide head from the suction foot portion; and (f) releasing the lead from the lead guide head; and (g) withdrawing the device from the pericardial region, whereby to leave the lead attached to the epicardial surface.

The present invention also includes a method for the thoracoscopic placement of a lead at a target site on an epicardial surface of a heart of a non-human animal, the method comprising: (a) extending into the pericardial region a device comprising: hollow lead guide; a lead extending through the hollow lead guide, the lead having a lead distal end portion; an elongated body having a longitudinal axis, a proximal end portion and a distal end portion, and having a proximal inlet and a distal lead outlet, the elongated body comprising (1) a lead receiving passageway for receiving and conducting the lead distal end to the distal lead outlet, and (2) a lumen adapted to provide suction to the distal end portion; a suction foot portion releasably attached to the lead distal end portion, and being in fluid communication with the lumen, the suction foot portion swivelably attached to the distal end portion such that the suction foot may be swiveled with respect to the longitudinal axis, and; the lead adapted to releasably engage the suction foot portion such that such engagement is of sufficient strength to maintain the position of the lead distal end portion as it engages the epicardial surface of a heart, and sufficiently releasable such that the lead may be released from the suction foot portion once the lead is attached to the epicardial surface of a heart; and an actuator extending from the proximal end portion to the distal end portion and adapted to tilt the suction foot portion about a first axis with respect to the longitudinal axis; wherein hollow lead guide is adapted to tilt the suction foot portion about a second axis with respect to the longitudinal axis; (b) positioning the suction foot portion upon the epicardial surface; (c) applying suction through the lumen so as to stabilize the suction foot against the epicardial surface; (d) inserting the lead distal end portion into the epicardial surface; (e) disengaging the lead from the suction foot portion; and (f) withdrawing the device from the pericardial region, whereby to leave the lead attached to the epicardial surface.

The present invention further includes a method for the placement of a conduit at a target site on a tissue surface of a non-human animal, the method comprising: (a) extending into the region of the tissue a device comprising: a hollow conduit guide having a conduit guide distal end, and connected to a conduit guide head at the conduit guide distal end; a conduit extending through the hollow conduit guide and having a conduit distal end portion, the conduit distal end portion extending from the conduit guide head for contact with the tissue surface, and releasably engaging the conduit guide head; an elongated body having a longitudinal axis, a proximal end portion and a distal end portion, and having a proximal inlet and a distal conduit outlet for extending the conduit guide head therethrough for contacting the conduit with the tissue surface, the elongated body comprising (1) a conduit receiving passageway for receiving and conducting the conduit guide head extending between the proximal inlet and the distal conduit outlet therethrough, and (2) a lumen adapted to provide suction to the distal end portion; a suction foot portion in fluid communication with the lumen, the suction foot portion tiltably attached to the distal end portion such that the suction foot may be tilted about two axes with respect to the longitudinal axis; the conduit guide head adapted to releasably engage the suction foot portion such that such engagement is of sufficient strength to maintain the position of the conduit as it engages the tissue surface, and sufficiently releasable such that the conduit guide head may be released from the suction foot portion once the conduit is attached to the epicardial surface of a heart; and an actuator extending from the proximal end portion and adapted to tilt the suction foot portion about a first of the axes; (b) positioning the suction foot portion upon the tissue surface; (c) applying suction through the lumen so as to stabilize the suction foot against the tissue surface; (d)

inserting the conduit distal end portion into the tissue surface; (e) disengaging the conduit guide head from the suction foot portion; and (f) releasing the conduit from the conduit guide head; and (g) withdrawing the device from the region of the tissue, whereby to leave the conduit attached to the epicardial surface.

Yet a further method of the present invention is a method for the placement of a conduit at a target site on a tissue surface of a non-human animal, the method comprising: (a) extending into the region of the tissue a device comprising: a hollow conduit guide; a conduit extending through the hollow conduit guide, the conduit having a conduit distal end portion; an elongated body having a longitudinal axis, a proximal end portion and a distal end portion, and having a proximal inlet and a distal conduit outlet, the elongated body comprising (1) a conduit receiving passageway for receiving and conducting the conduit distal end to the distal conduit outlet, and (2) a lumen adapted to provide suction to the distal end portion; a suction foot portion releasably attached to the conduit distal end portion, and being in fluid communication with the lumen, the suction foot portion swivelably attached to the distal end portion such that the suction foot may be swiveled with respect to the longitudinal axis, and; the conduit adapted to releasably engage the suction foot portion such that such engagement is of sufficient strength to maintain the position of the conduit distal end portion as it engages the tissue surface, and sufficiently releasable such that the conduit may be released from the suction foot portion once the conduit is attached to the tissue surface; and an actuator extending from the proximal end portion to the distal end portion and adapted to tilt the suction foot portion about a first axis with respect to the longitudinal axis; wherein hollow conduit guide is adapted to tilt the suction foot portion about a second axis with respect to the longitudinal axis; (b) positioning the suction foot portion upon the tissue surface; (c) applying suction through the lumen so as to stabilize the suction foot against the tissue surface; (d) inserting the conduit distal end portion into the tissue surface; (e) disengaging the conduit from the suction foot portion; and (f) withdrawing the device from the tissue region; whereby to leave the conduit attached to the tissue surface.

The foregoing and other objects, features, and advantages of this invention will become more readily apparent from the following detailed description of a preferred embodiment which proceeds with reference to the accompanying drawings, wherein the preferred embodiment of the invention is shown and described, simply by way of illustration of the best mode contemplated of carrying out the invention.

As will be realized, the invention is capable of other and different embodiments, and its several details are capable of modifications in various obvious respects, all without departing from the invention. Accordingly, the drawings and description are to be regarded as illustrative in nature, and not as restrictive. It will also be appreciated that the detailed description represents the preferred embodiment of the invention, and that individual steps of the process of the invention may be practiced independently so as to achieve similar results.

DETAILED DESCRIPTION OF THE PREFERRED EMBODIMENTS

In accordance with the foregoing summary, the following provides a detailed description of the preferred embodiment, which is presently considered to be the best mode thereof.

Figure 1:
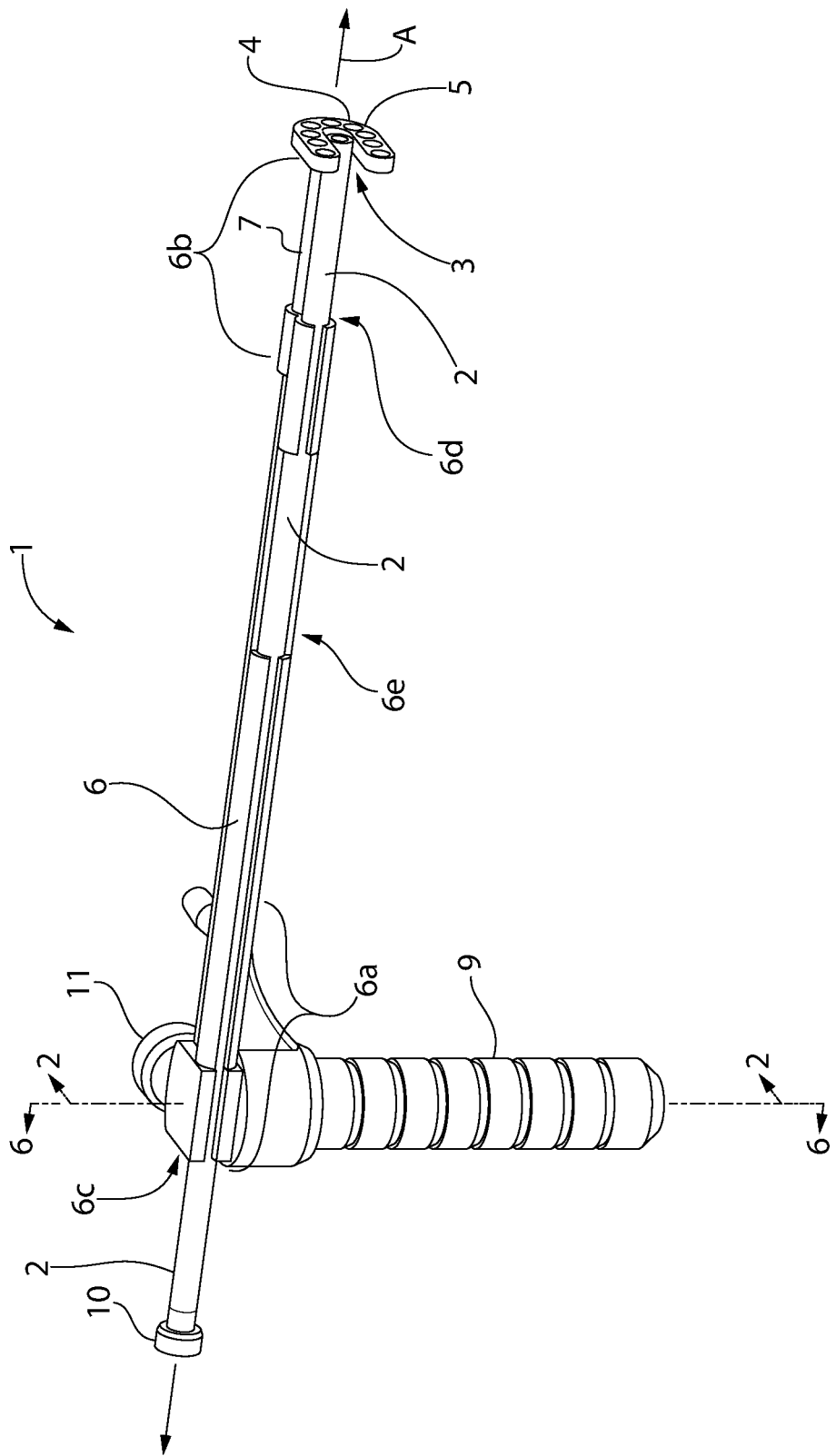
FIG. 1 is a first side lateral perspective view of a device in accordance with one embodiment of the present invention.
Figure 2:
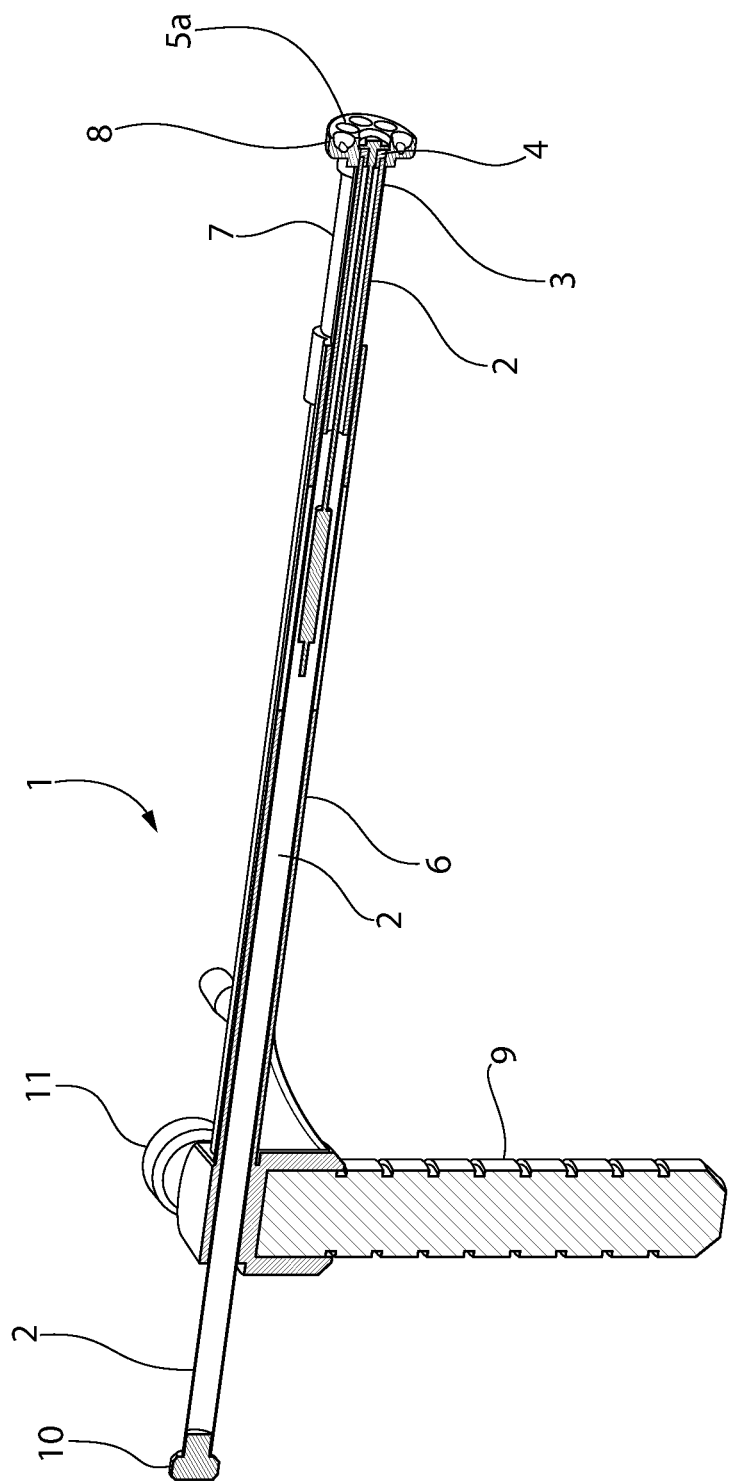
FIG. 2 is a sectioned first side lateral perspective view of a device in accordance with one embodiment of the present invention, taken along line 2-2 of FIG. 1.

FIG. 1 is a first side lateral perspective view of a device in accordance with one embodiment of the present invention, and FIG. 2 shows a sectioned first side lateral perspective view of the device 1, taken along line 2-2 of FIG. 1.

FIG. 1 shows a device 1 adapted for the thoracoscopic placement of a lead at a target site on an epicardial surface of a heart (that being its principal, but non-exclusive mode of use), the device 1 comprising: (a) a hollow lead guide 2 having a lead guide distal end 3, and connected to a lead guide head 4 at the lead guide distal end 3; (b) a lead 5 extending through the hollow lead guide 2 and having a lead distal end portion 5a, the lead distal end portion 5a extending from the lead guide head 4 for contact with the epicardial surface of the heart, and releasably engaging the lead guide head 4; (c) an elongated body 6 having a longitudinal axis A, a proximal end portion (generally 6a) and a distal end portion (generally 6b), and having a proximal inlet 6c and a distal lead outlet 6d for extending the lead guide head 4 therethrough for contacting the lead 5 with the epicardial surface of the heart. The elongated body 6 also has an optional port 6e that allows the operator to guide the lead guide distal end 3 though the elongated body 6.

Figure 7:
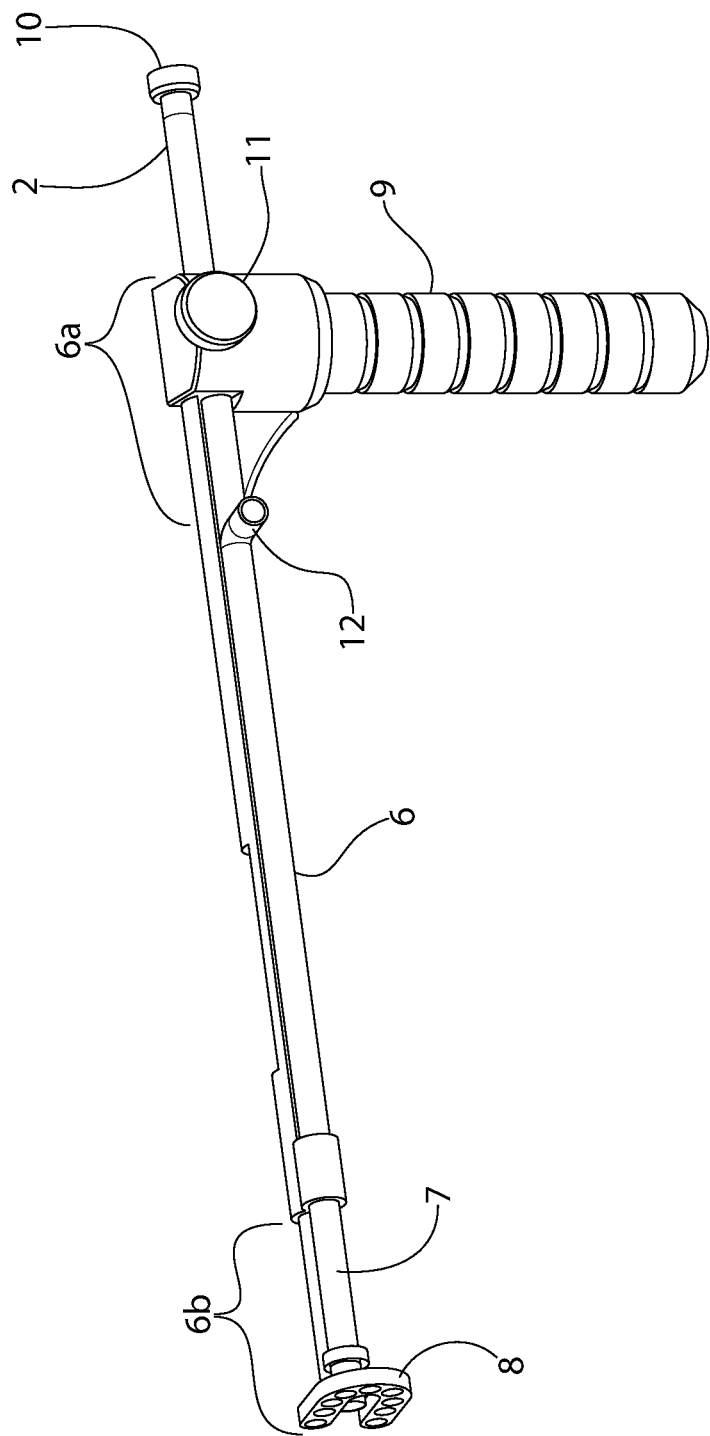
FIG. 7 is a second side lateral perspective view of a device in accordance with one embodiment of the present invention.

FIG. 7 is a second side lateral perspective view of a device 1, and in which like reference numerals refer to corresponding portions thereof.

The elongated body 6 comprises (1) a lead receiving passageway (defined in part of elongated body 6) for receiving and conducting the lead guide head 4, and extending between the proximal inlet and the distal lead outlet therethrough; and (2) a lumen 7 adapted to provide suction to the distal end portion thereof.

Figure 3:
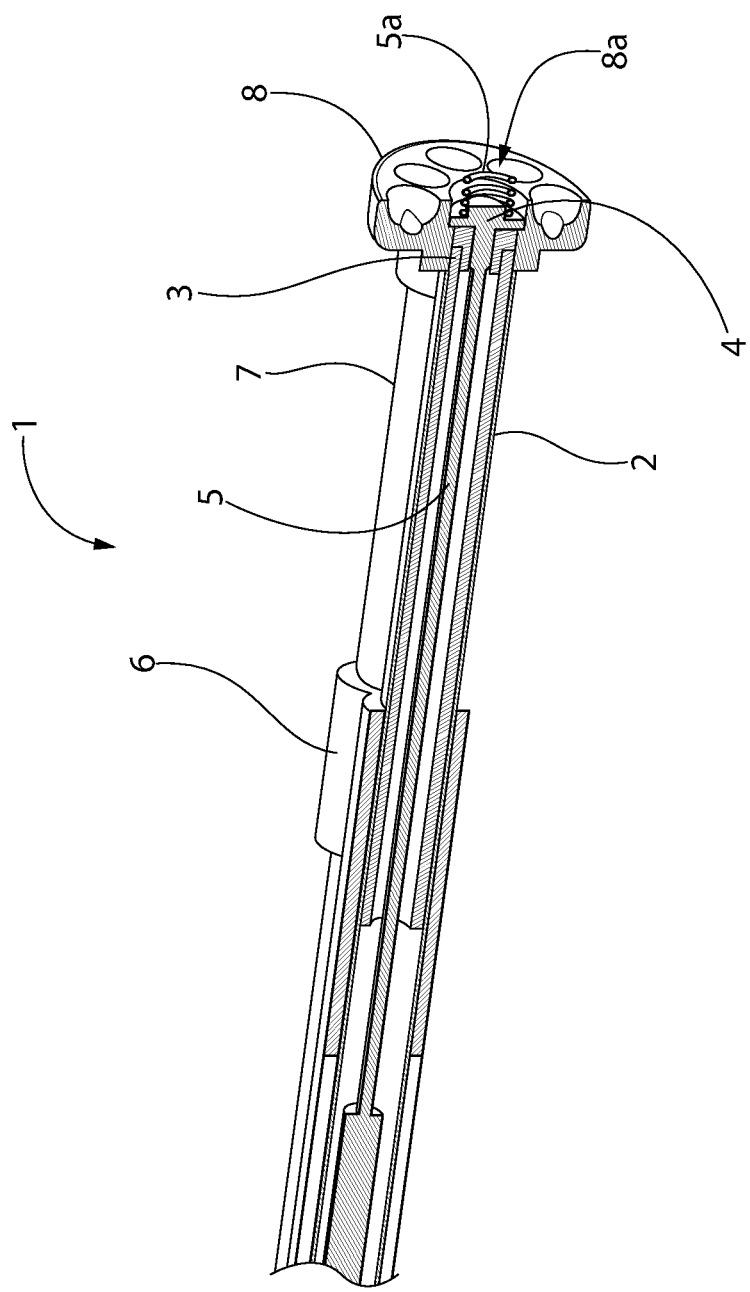
FIG. 3 is a detailed sectioned first side lateral perspective view of a device in accordance with one embodiment of the present invention, taken along line 2-2 of FIG. 1, as shown more generally in FIG. 2.

FIG. 3 shows a detailed sectioned first side lateral perspective view of the device 1, taken along line 2-2 of FIG. 1. This view better shows the distal end of the device 1, with suction foot portion 8 is in fluid communication with the lumen 7.

Figure 8:
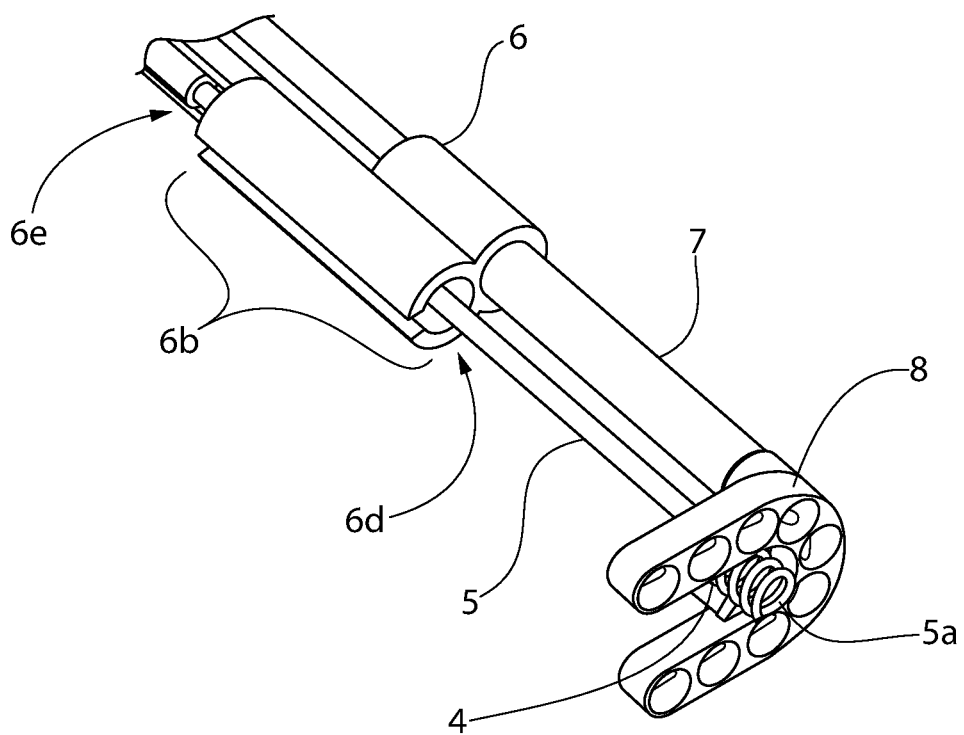
FIG. 8 is a detailed upper first side lateral perspective view of the distal end of a device in accordance with one embodiment of the present invention.

FIG. 8 is a detailed upper first side lateral perspective view of the distal end of a device 1, and in which like reference numerals refer to corresponding portions thereof. This Figure shows the distal lead outlet 6d for extending the lead guide head 4 therethrough for contacting the lead 5 with the epicardial surface of the heart. This Figure also shows the appearance of the device 1 with hollow lead guide 2 removed so as to show the lead 5 extending through elongated body portion 6 to reach the lead guide head 4 held in suction foot portion 8 and from which it presents lead distal end portion 5a, with the lead distal end portion 5a extending from the lead guide head 4 for contact with the epicardial surface of the heart.

Figure 9:
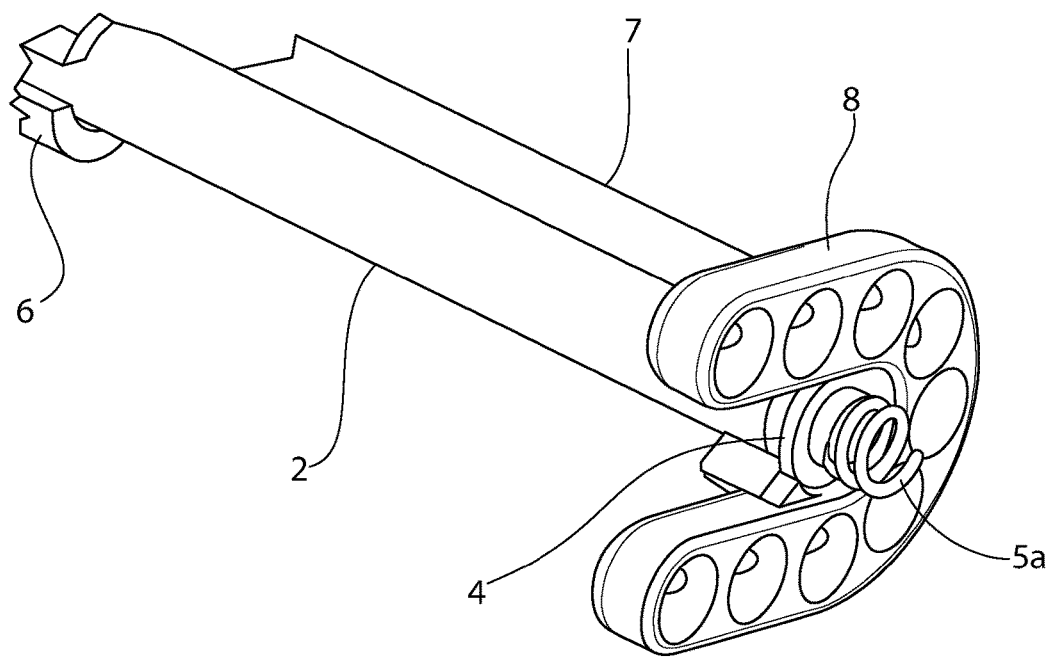
FIG. 9 is a more detailed upper first side lateral perspective view of the distal end of a device in accordance with one embodiment of the present invention, as shown more generally in FIGS. 1 and 8.
Figure 10:
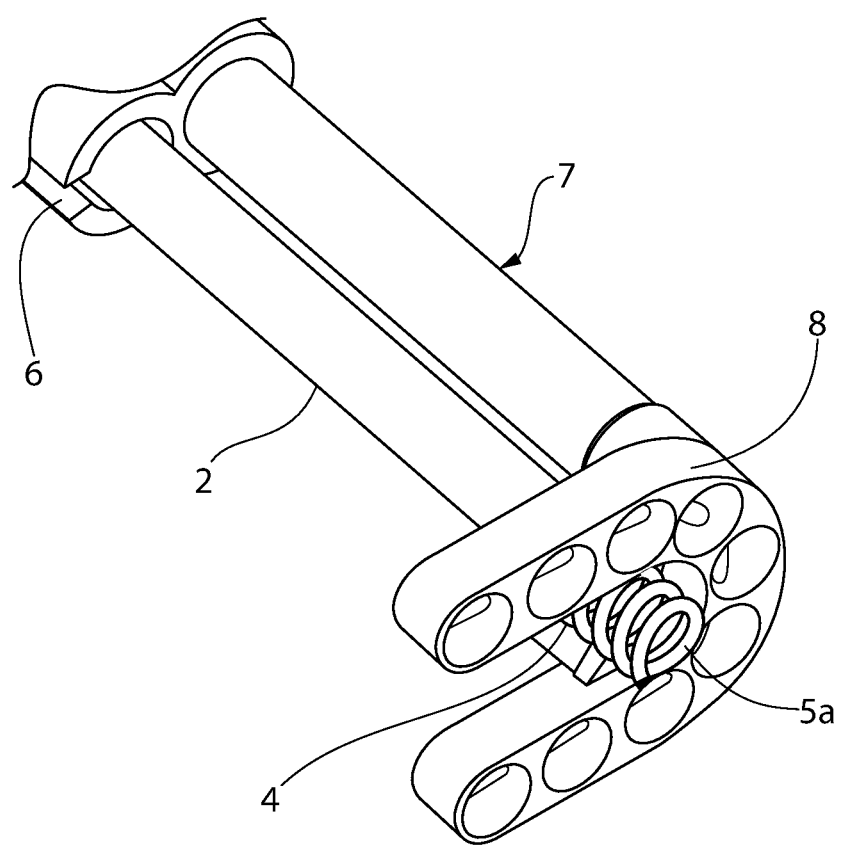
FIG. 10 is a highly detailed upper first side lateral perspective view of the distal end of a device in accordance with one embodiment of the present invention as shown more generally in FIGS. 1, 8 and 9.

FIG. 9 is a more detailed upper first side lateral perspective view of the distal end of a device 1, as shown more generally in FIGS. 1 and 8, and in which like reference numerals refer to corresponding portions thereof. This Figure also shows the appearance of the device 1 with hollow lead guide 2 in place as would be seen as it contains lead 5 extending also passing through elongated body portion 6 to reach the lead guide head 4 held in suction foot portion 8 and from which it presents lead distal end portion 5a, with the lead distal end portion 5a extending from the lead guide head 4 for contact with the epicardial surface of the heart. FIG. 10 is an even more detailed upper first side lateral perspective view of the distal end of a device 1, as shown more generally in FIGS. 1, 8 and 9, and in which like reference numerals refer to corresponding portions thereof.

Figure 4:
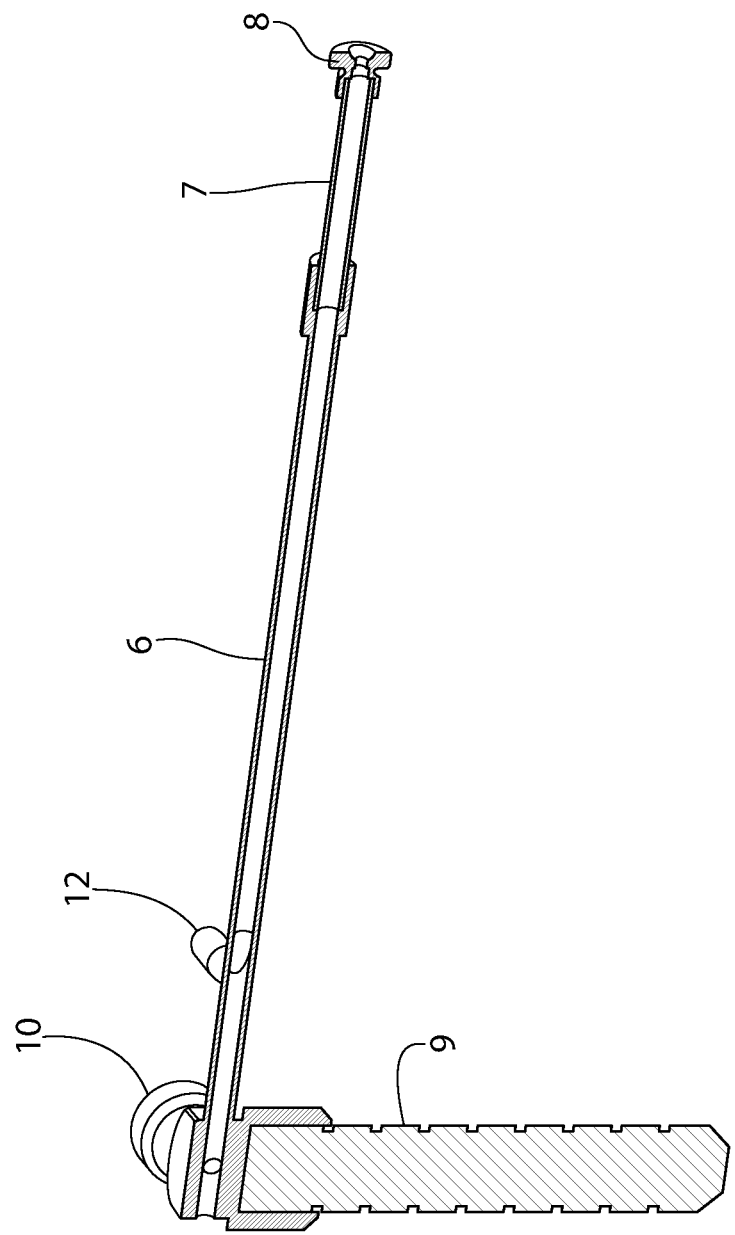
FIG. 4 is a sectioned lateral perspective view of an elongated body portion of the device shown in FIG. 2, as would be seen if likewise sectioned along the same line 2-2 in FIG. 2, in accordance with one embodiment of the present invention.
Figure 5:
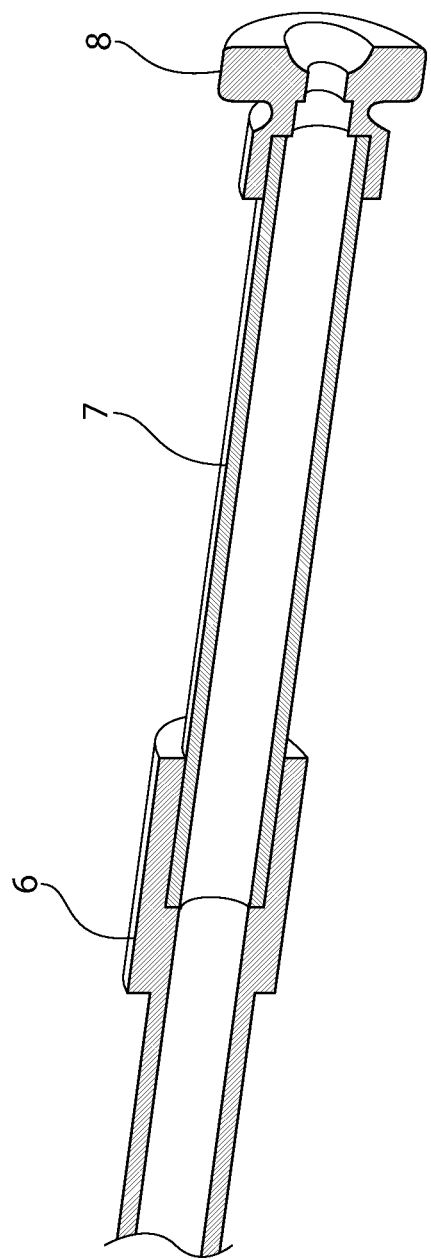
FIG. 5 is a detailed sectioned first side lateral perspective view of an elongated body portion of the device in accordance with one embodiment of the present invention, shown more generally in FIG. 4.

FIG. 4 is a sectioned lateral perspective view of an elongated body portion 6 of the device 1 shown in FIG. 2, and FIG. 5 is a detailed sectioned first side lateral perspective view of an elongated body 6, both showing the suction foot portion 8 is in fluid communication with the lumen in greater detail. The lumen 7 typically will comprise a plastic tube, and will typically be sufficiently flexible to permit the suction foot portion 8 to swivel in connection therewith at the distal end. The balance of the lumen 7 may be formed by one or more other lengths of plastic tube, and portions may be comprised by tubular portions of the elongated body 6 itself, as may be appreciated from FIG. 5. The lumen 7 may be served by a source of vacuum as described herein such as at vacuum port 12.

The suction foot portion 8 tiltably or swivelably attached to the distal end portion of the elongated body 6 such that the suction foot may be tilted or swiveled about two axes with respect to the longitudinal axis A, to permit the suction foot portion 8 to be positioned for most effective lead placement. This attachment is shown in greater detail in FIGS. 13-23 that describes the preferred embodiment incorporating a spring.

The lead guide head 4 is configured so as to be releasably engaged with the suction foot portion 8 such that such engagement is of sufficient strength to maintain the position of the lead distal end 5a portion as it engages the epicardial surface of a heart, and sufficiently releasable such that the lead guide head 4 may be released from the suction foot portion 8 once the lead 5 is attached to the epicardial surface of a heart); and (e) an actuator extending from the proximal end portion to the distal end portion and adapted to tilt the suction foot portion about a first of the axes.

The elongated body 6 may be of any length, but typically will have a lead receiving passageway that has a length in the range of 10 cm to 40 cm for manually actuated devices. Robotic adaptation of the present invention may use shorter lengths as well.

It is preferred that the elongated body 6 of manually actuated devices be provided with a handle portion 9 extending laterally therefrom for ease of manual use, though it will be appreciated that the invention may be adapted for robotic use without need of a handle.

It is also preferred that the device be provided with a knob 10 so as to permit the hollow lead guide 2 to be rotated within the elongated body 6 by hand, so as to rotate the lead guide head 4, to permit the user to urge or twist the lead into place, especially where the distal end of the lead wire 5a is in a corkscrew shape as is common.

In the preferred variant of the present invention is a lead placement device with a suction foot 8 and releasable lead 5, optional releasable lead head 4, with an actuator (shown in FIGS. 13-23) that permits the suction foot 8 and releasable lead 5, with optional releasable lead head, to be swiveled about a second axis. In this variation, the hollow lead guide additionally and preferably comprises a flexible member connecting the lead guide head to the lead guide distal end, and this flexible member may be any part of sufficient flexibility and resilience to permit the lead guide head and the suction foot 8 to swivel as described herein. For instance the flexible member may be in the form of a metal or plastic spring, or equivalent metal or plastic structure.

In a most preferred embodiment the flexible member is of sufficient stiffness in the longitudinal direction (such as with a metal spring), that, upon movement of the hollow lead guide 2 within the elongated body 6, the suction foot portion 8 may be tilted or swiveled in a first direction axis. In this most preferred embodiment the suction foot portion 8 has an engagement aperture 8a aligned with the hollow lead guide 2, and wherein the lead guide head 4 is adapted to releasably engage with the engagement aperture 8a, such as where the suction foot portion 8 and lead guide head 4 are made of a plastic material, and are sized so as to provide a light mechanical interferences fit that may be released through longitudinal hand force. This releasable engagement may be accomplished by any other means acceptable to the device's use, such as through the use of light magnetic forces or adhesives, as well as through the use of mechanical arrangements involving light interferences fits, that are both of sufficient strength to permit the suction foot 8 to be swiveled into the desired position, while allowing the suction foot 8 and the balance of the device 1 to be pulled free after final lead placement. This permits the lead guide to function both to assist in swiveling the suction foot 8, and the lead 5 it holds, into position on the heart or other tissue surface, while also holding the lead 5 in position for optional lead testing and ultimate lead placement, followed by release of the suction foot 8 (along with the balance of the device), following final lead placement.

Figure 6:
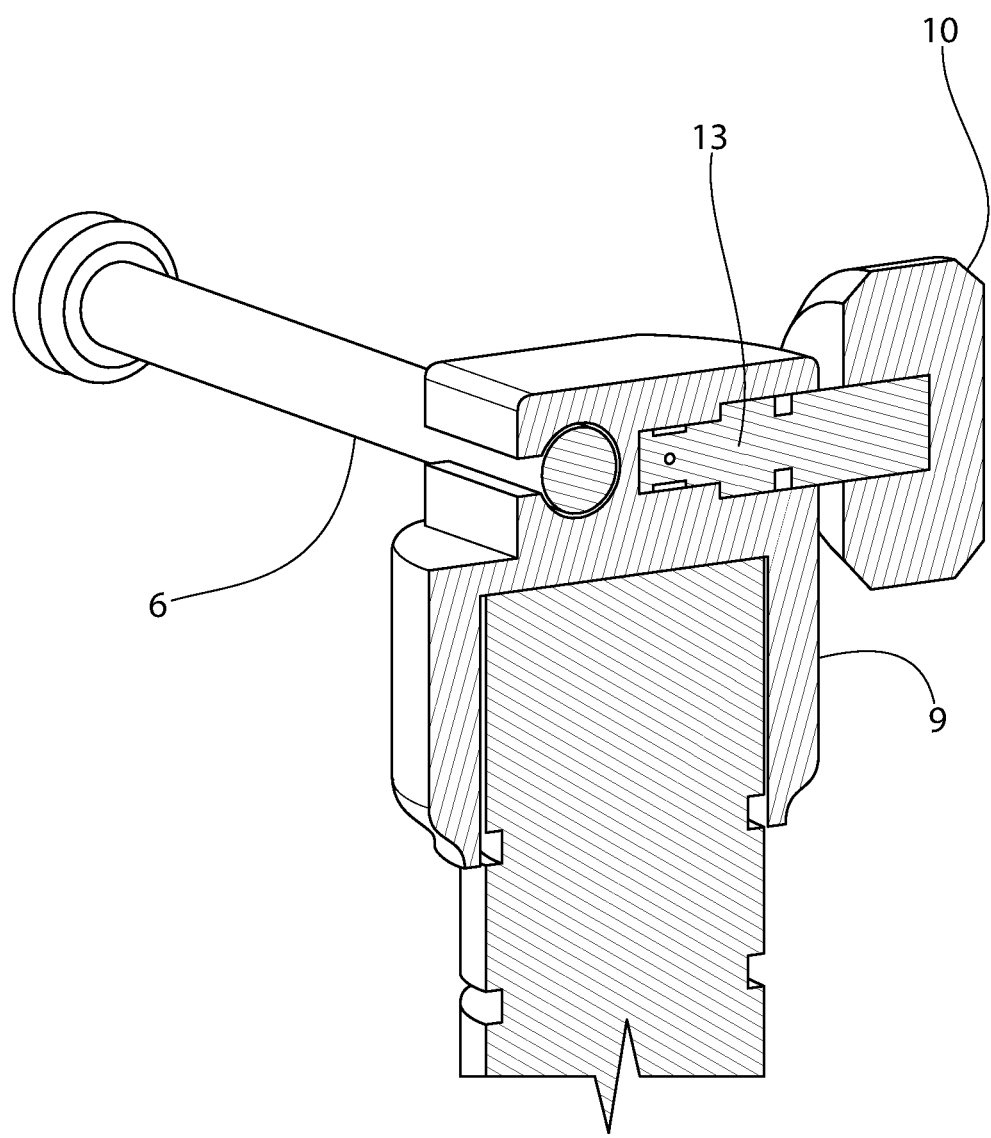
FIG. 6 is a detailed sectioned proximal end perspective view of an elongated body portion of the device sectioned along the same line 6-6 in FIG. 2, in accordance with one embodiment of the present invention.

It is also preferred that the device be provided with a knob 11 that moves the actuator to allow the operator to reciprocally move the actuator within the elongated body 6 by hand, so as tilt and swivel the suction foot 8 in a second direction. FIG. 6 is a detailed sectioned proximal end perspective view of an elongated body portion 6 of the device sectioned along the same line 6-6 in FIG. 2, and showing the position of a winding portion integrated near the handle portion 9 about which an actuator, such as a metal wire, may be wound so as to be reciprocally moved within the elongated body portion 6 in accordance with one embodiment of the present invention.

Accordingly, through the cooperative movement of the hollow lead guide 2 within the elongated body 6 using knob 10, and the reciprocally move the actuator within the elongated body 6 using knob 11, the operator may move and swivel the suction foot 8 in different directions through a range of motion that, together with accessory turning of the device 1 itself about its longitudinal axis A, allows the operator to position and orient the suction foot 8 substantially normal to the desired target tissue surface.

Figure 11:
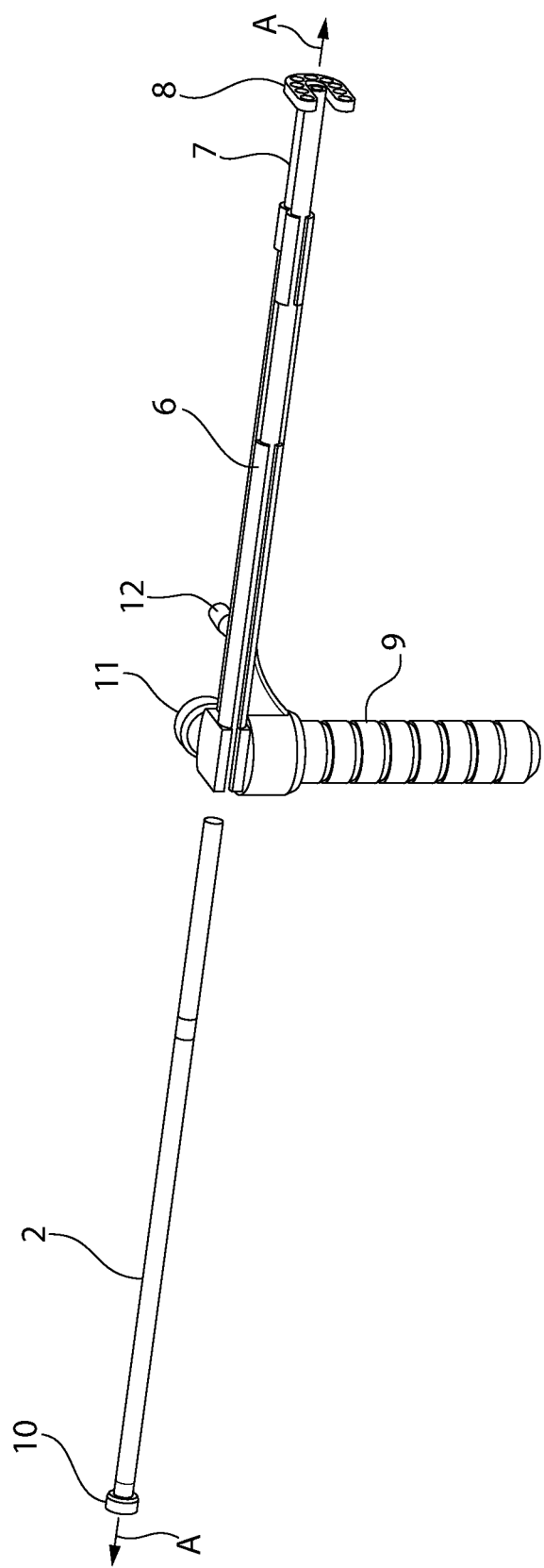
FIG. 11 is an exploded first side lateral perspective view of a device in accordance with one embodiment of the present invention.

FIG. 11 is an exploded first side lateral perspective view of a device 1, and in which like reference numerals refer to corresponding portions thereof. This Figure shows how the of the hollow lead guide 2 is extended through the elongated body 6 to reach the suction foot portion 8 that may be tilted or swiveled in a first direction axis through its reciprocating movement along the longitudinal axis. In this embodiment, the attachment of the lumen acts as a counterbalance to that movement, as well as optionally being the conduit for the actuator that also acts upon the suction foot portion 8 to tilt or swivel it in a second direction.

Figure 12:
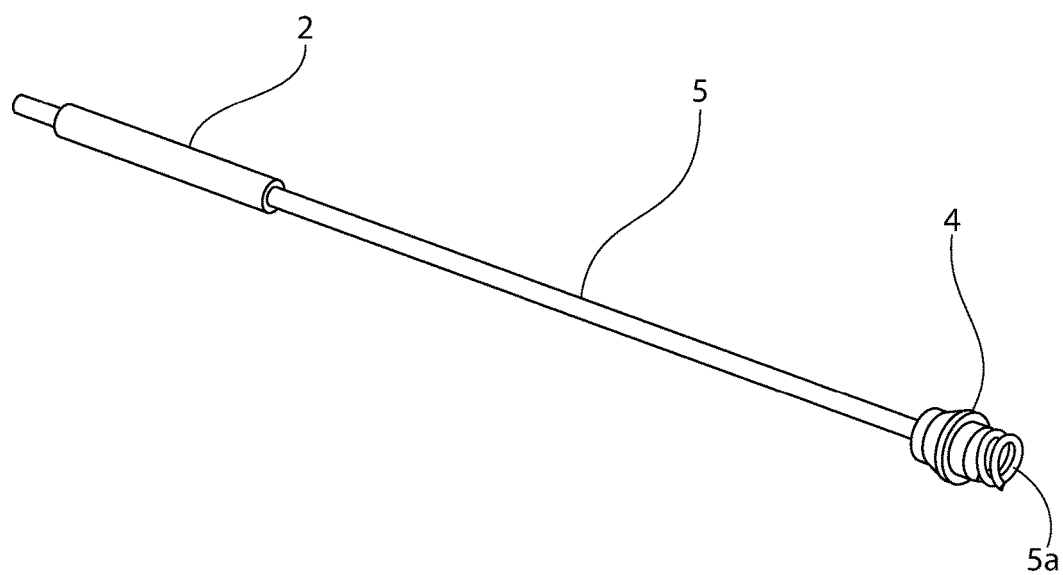
FIG. 12 is a lateral perspective view of a lead guide portion of the device shown in FIGS. 1 and 11, in accordance with one embodiment of the present invention.

FIG. 12 is a lateral perspective view of a lead guide portion of the device shown in FIGS. 1 and 11, and in which like reference numerals refer to corresponding portions thereof.

FIGS. 13-23 show a more detailed depiction of the preferred embodiment of the distal end of a device 1 of the present invention, and in which like reference numerals refer to corresponding portions thereof.

Figure 13:
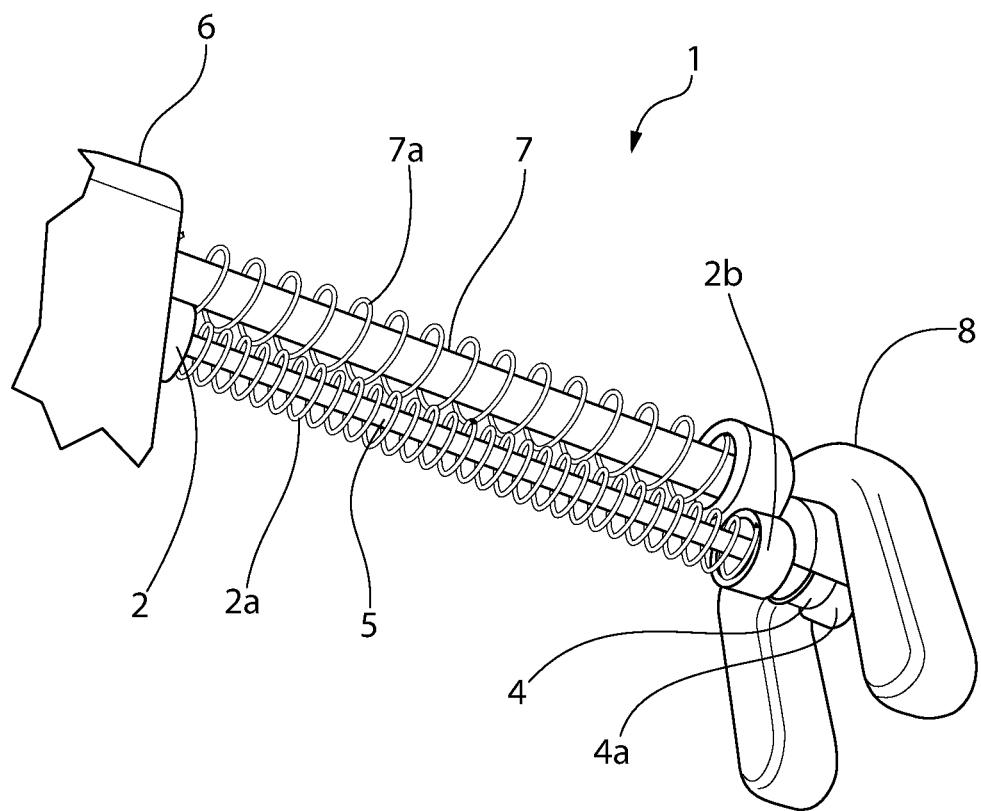
FIG. 13 is a depiction showing an upper first side lateral perspective view of the distal end of a device in accordance with one embodiment of the present invention.

FIG. 13 shows a detailed view of the distal end of a device 1 one of the preferred embodiment of the present invention. FIG. 13 shows the distal end of the elongated body portion 6 which supports and directs hollow lead guide 2 in its reciprocal action along the longitudinal axis of the device as show in earlier Figures. From the end of the hollow lead guide 2, a spring 2a extends reaching to a flange 2b that in turn is attached lead guide head 4. The cardiac lead 5 extends from the end of the hollow lead guide 2 through the spring 2a to reach the lead guide head 4. In this embodiment, the lead guide head 4 is attached to the end of the cardiac lead 5a through the use of an additional sleeve portion 4a through which the cardiac lead 5 extends to present corkscrew shape on the distal side of sleeve portion 4a (as seen in subsequent Figures). FIG. 13 also shows lumen 7 extending from the distal end of the elongated body portion 6 to a fluid connection with suction foot portion 8. Lumen 7 extends through spring 7a.

Springs 2a and 7a thus cooperate to permit suction foot portion 8 to swivel either through motion of the hollow lead guide 2 to which spring 2a is attached or by action of the actuator that extends through lumen 7 (or otherwise) to be able to push against suction foot portion 8 (or physical structure attached thereto), or conversely to pull upon suction foot portion 8 in the opposite direction. In this way, suction foot portion 8 may be turned and swiveled to bring it substantially parallel to the intended target plane, and thereby to bring lead distal end 5a substantially normal to the intended target site.

Figure 14:
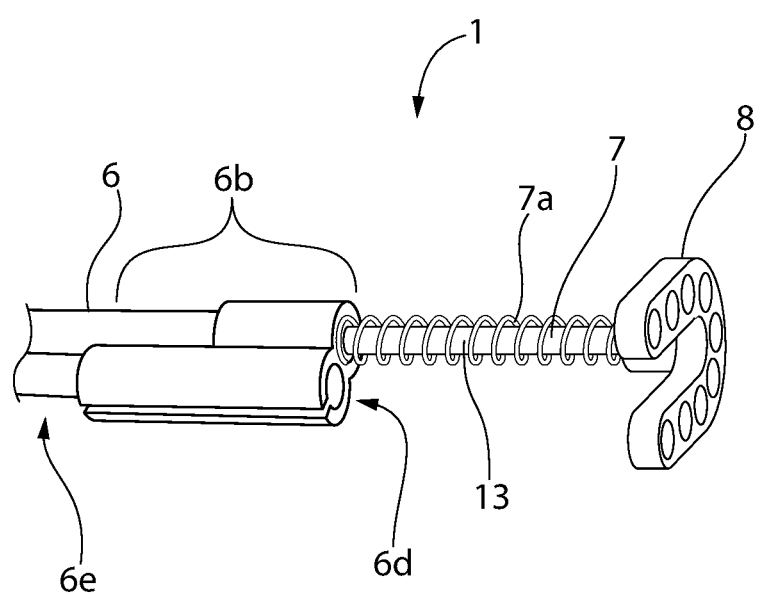
FIG. 14 is a depiction showing another upper first side lateral perspective view of the distal end of a device in accordance with one embodiment of the present invention.

FIG. 14 is a depiction showing another upper first side lateral perspective view of the distal end of a device 1 of the present invention, and in which like reference numerals refer to corresponding portions thereof. FIG. 14 shows the device 1 of the present invention with the hollow lead guide 2 removed to show more clearly the elongated body portion distal outlet 6(d) and the lateral port 6(e). In this Figure, one can also see the position of the actuator 13 extending lumen 7 which, by reciprocating motion in connection with suction foot portion 8, brings about the tilting of suction foot portion 8.

Figure 15:
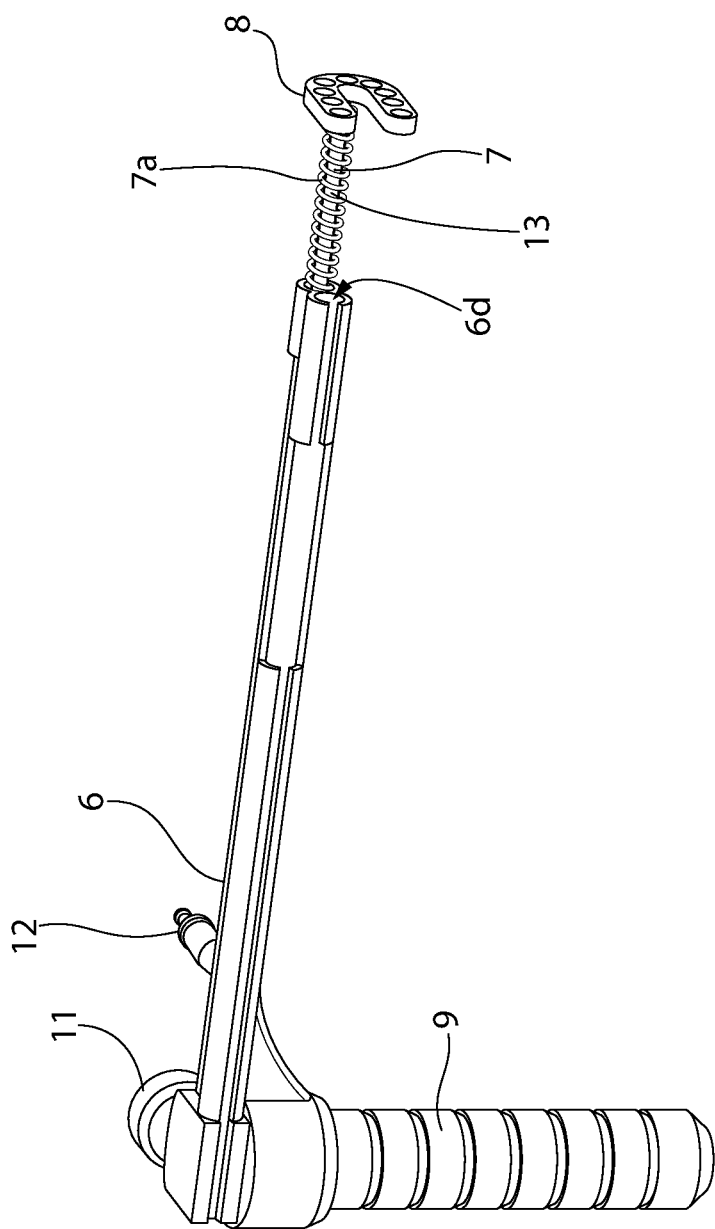
FIG. 15 is a depiction showing another upper first side lateral and distal end perspective view of the distal end of an elongated body portion and suction head of the device in accordance with one embodiment of the present invention.

FIG. 15 is a depiction showing another upper first side lateral and distal end perspective view of the distal end of an elongated body portion and suction head of the device 1 of the present invention, and in which like reference numerals refer to corresponding portions thereof. FIG. 15 shows a more complete perspective view of the device shown in FIG. 14 and wherein the relative position of the elongated body portion 6, its handle 9, actuator knob 11 and vacuum port 12 can be appreciated. This view also shows elongated body portion distal opening 6(d), as well as lumen 7 extending from the elongated body portion 6 and containing actuator 13 while being swivelably supported by spring 7a.

Figure 16:
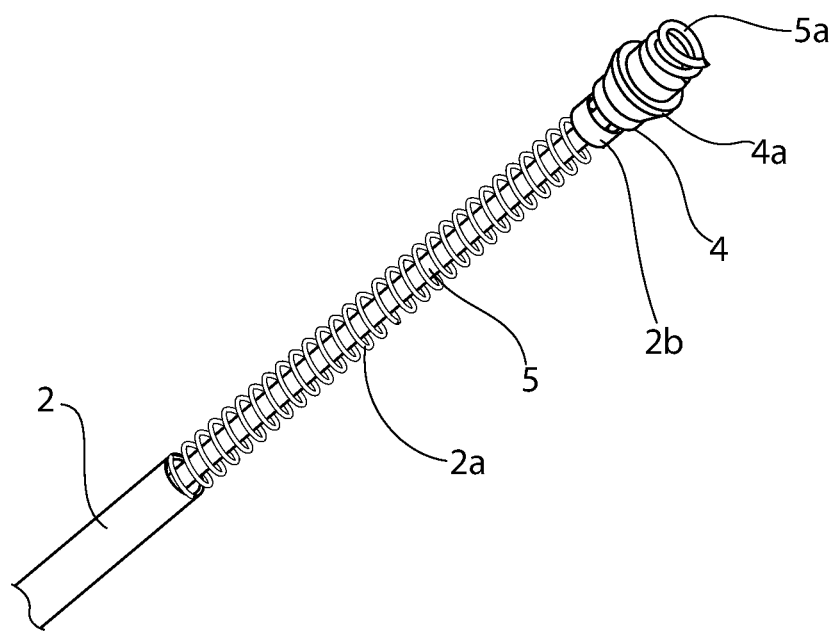
FIG. 16 is a depiction showing another upper first side lateral and distal end perspective view of the distal end of a lead guide portion of the device in accordance with one embodiment of the present invention.

FIG. 16 is a depiction showing another upper first side lateral and distal end perspective view of the distal end of a lead guide portion of the device 1 of the present invention, and in which like reference numerals refer to corresponding portions thereof. FIG. 16 is a depiction of the hollow lead guide 2 from which extends spring 2a to optional sleeve portion 2b. The optional sleeve portion 2b or other portion of the lead guide head 4, may be used to engage the suction foot portion 8, in this case between the legs of its horseshoe shape. This view further shows spring 2a in connection with lead guide head 4 which in turn releasably supports sleeve 4a into which lead 5 is connected. This view shows that, once lead distal end 5a is placed into the tissue such as through a turning of knob 10, the lead remains in place with sleeve portion 4a, while allowing the guide head 4 to be withdrawn along with the balance of the lead guide structure.

Figure 17:
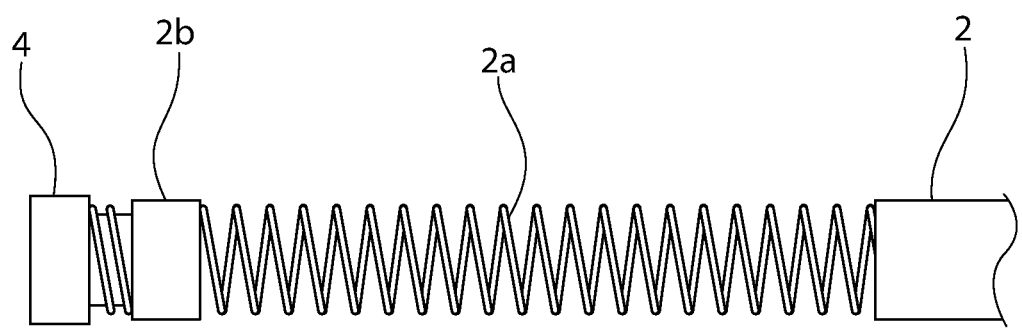
FIG. 17 is a depiction showing a first side lateral view of the distal end of a lead guide portion of the device in accordance with one embodiment of the present invention.
Figure 18:
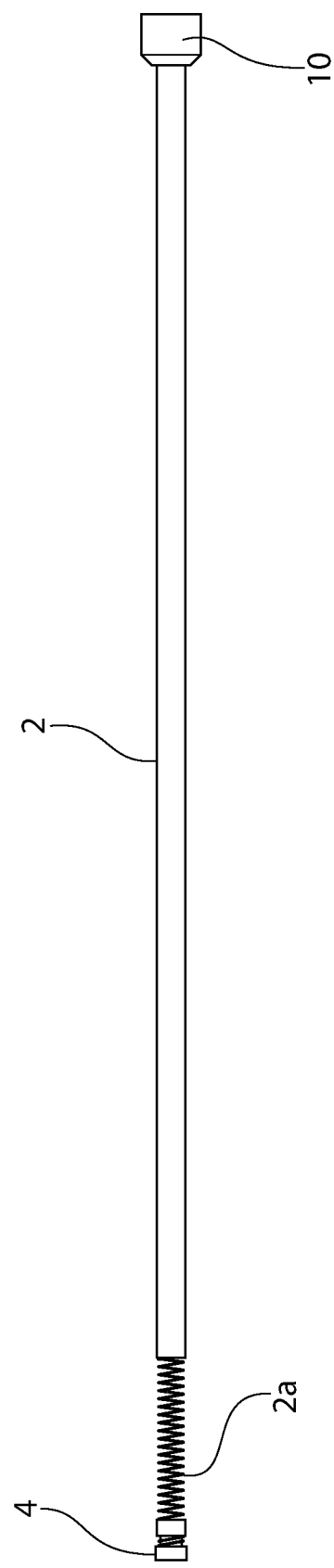
FIG. 18 is a depiction showing a first side lateral view of a lead guide portion of the device in accordance with one embodiment of the present invention.
Figure 19:
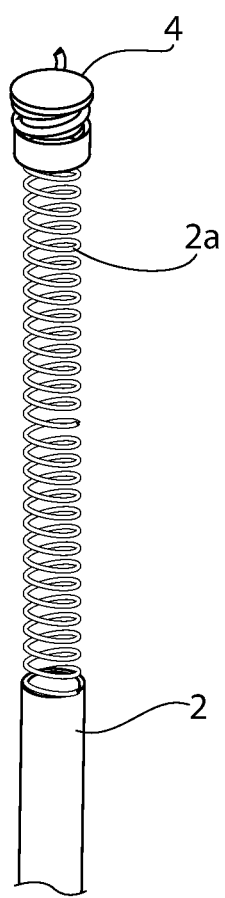
FIG. 19 is a depiction showing a distal end perspective view of the distal end of a lead guide portion of the device in accordance with one embodiment of the present invention.

FIGS. 17 and 18 are depictions showing a first side lateral view of the distal end of a lead guide portion of the device 1 of the present invention, and in which like reference numerals refer to corresponding portions thereof. FIG. 19 is a depiction showing a distal end perspective view of the distal end of a lead guide portion of the device 1 of the present invention, and in which like reference numerals refer to corresponding portions thereof.

Figure 20:
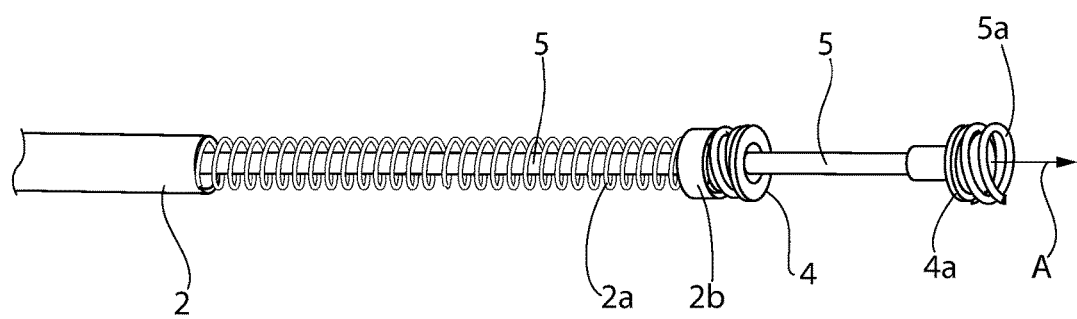
FIG. 20 is a depiction showing a first side lateral view of the distal end of a lead guide portion of the device in accordance with one embodiment of the present invention.

FIG. 20 is a depiction showing a first side lateral view of the distal end of a lead guide portion of the device 1 of the present invention, and in which like reference numerals refer to corresponding portions thereof. FIG. 20 shows the lead guide portion of the device with the lead 5, sleeve 4a and lead distal end 5a disengaged from lead guide head 4 and the balance of the lead guide portion, as would occur as the lead guide portion is withdrawn from the target area after placement of the lead distal end 5a, such as by withdrawing it along longitudinal axis A.

Figure 21:
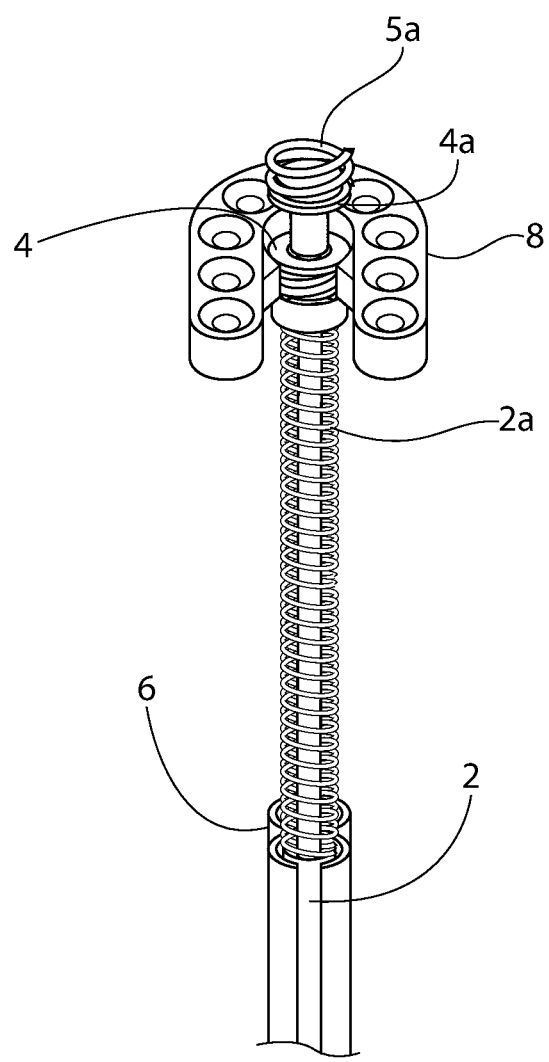
FIG. 21 is a depiction showing a distal end perspective view of the distal end of a lead guide portion and suction head of the device in accordance with one embodiment of the present invention.

FIG. 21 is a depiction showing a distal end perspective view of the distal end of a lead guide portion and suction head of the device 1 of the present invention, and in which like reference numerals refer to corresponding portions thereof. FIG. 21 shows a detailed distal end perspective view of the device 1, and shows how lead guide head 4 may be configured so as to fit into a corresponding structure in suction foot 8 to allow suction foot 8 to be swiveled by action of the hollow lead guide 2, while also being adapted to permit sleeve 4a to disengage from lead guide head 4 to allow the suction foot and associated lead guide head to disengage from the sleeve 4a and the lead distal end 5a once the lead is placed.

Figure 22:
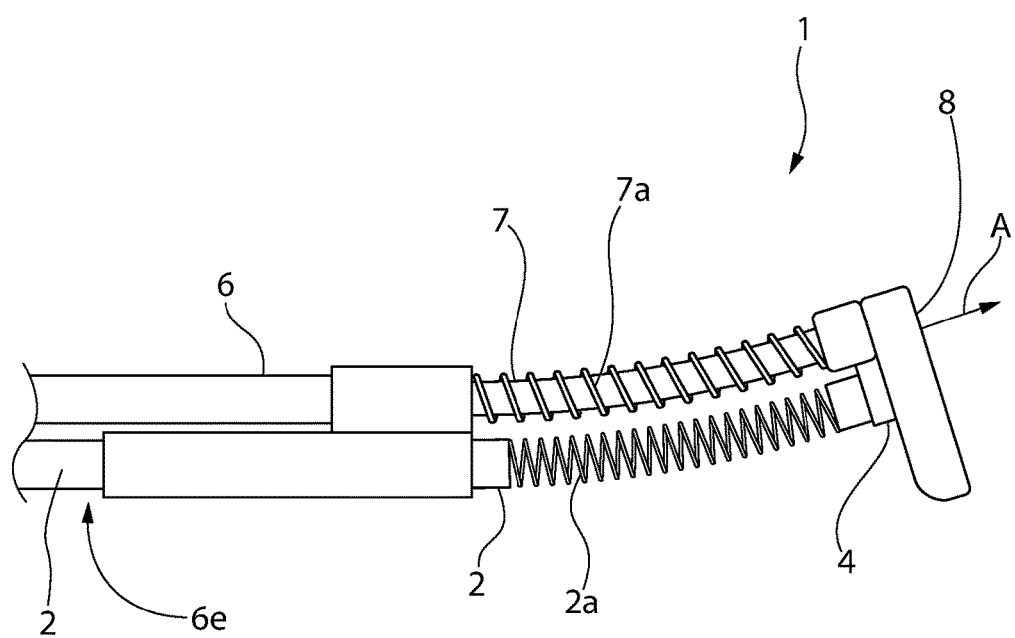
FIG. 22 is a depiction showing an upper first side lateral perspective view of the distal end of a device in accordance with one embodiment of the present invention.

FIG. 22 is a depiction showing an upper first side lateral perspective view of the distal end of a device 1 of the present invention, and in which like reference numerals refer to corresponding portions thereof. FIG. 22 shows still another view of the distal end of the device 1 following displacement of the lead 5 having been drawn substantially along longitudinal axis A.

Figure 23:
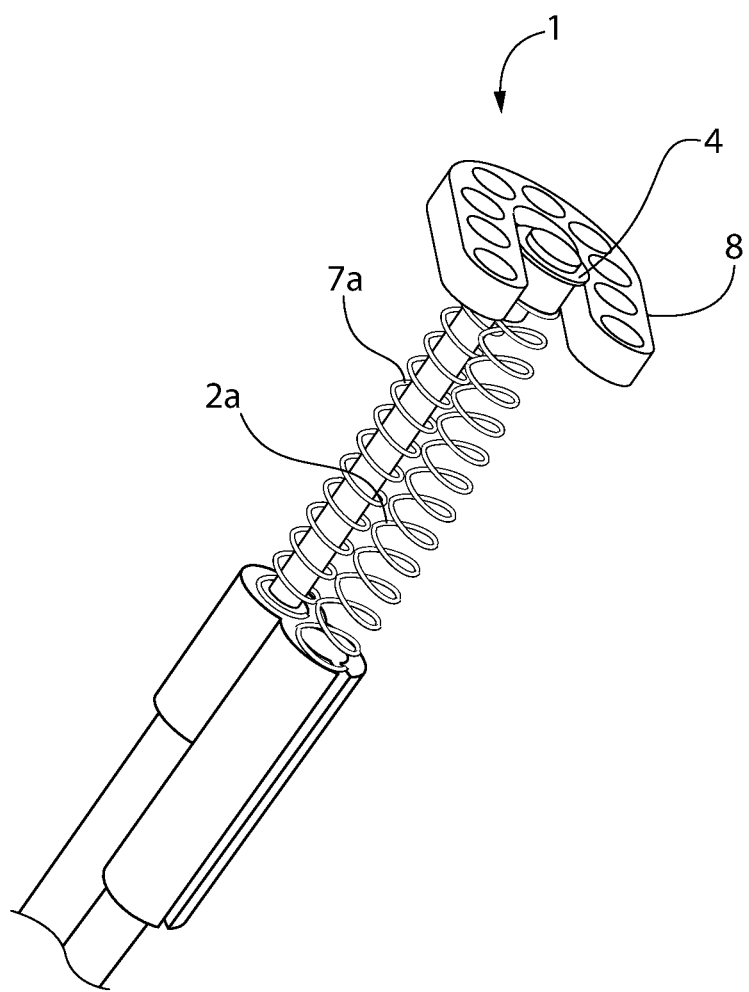
FIG. 23 is a depiction showing another upper first side lateral perspective view of the distal end of a device in accordance with one embodiment of the present invention.

FIG. 23 is a depiction showing another upper first side lateral perspective view of the distal end of a device 1 of the present invention, and in which like reference numerals refer to corresponding portions thereof. FIG. 23 shows an end view of the device 1 of the present invention and showing the distal end of the device as it would appear following displacement of the lead and withdrawal of the balance of the device from the target site.

In order to operate the device of the present invention, the hollow lead guide 2 is placed into and through the elongated body portion 6, and this may be facilitated by guiding the hollow lead guide 2 bearing spring 2a, optional sleeve portion 2b and lead guide head 4 through the elongated body portion 6, which access may be facilitated by use of optional port 6e. After the hollow lead guide 2 is passed from the proximal end 6a to the distal 6b through distal opening 6d, the distal end of the hollow lead guide 2 (i.e., the lead guide head 4 and/or optional sleeve portion 2b, are seated in the suction foot portion 8 so as to permit the lead 5 it will guide to extend beyond the plane defined by the contact side of the suction foot portion 8). The lead 5 may then be affixed into the lead guide head by extending the lead 5 into the lead guide head until, in the preferred embodiment, sleeve 4a releasably engages into lead guide head 4.

With the lead 5 in place, a source of suction, such as a 10 cc or 20 cc syringe may be affixed to vacuum port 12. This mode of construction is preferred where the surgeon desires to be free of any tether to wall-mounted vacuum ports.

In order to place the lead, the distal end of the device 1 is inserted into the patient directed toward the target site. In its rest position, the suction foot portion 8 typically is in a position such that the contact plane is substantially perpendicular to the longitudinal axis of the device. As the device is moved toward the target tissue or organ (such as the heart), turning the knob 11 in alternating directions will cause the contact plane of the suction foot portion 8 to deflect in respective alternate directions with respect to the vertical (i.e., in this embodiment with respect to the axis defined by the handle portion 9). By contrast, small reciprocal movements of the hollow guide portion 2 within the elongated body portion 6 will cause the contact plane of the suction foot portion 8 to be respectively deflected with respect to the perpendicular or "horizontal" axis. This movement may be brought about by small push and pull movements of knob 10. In this way, the surgeon may combine these movements to swivel the suction foot portion 8 target plane to the desired attitude with respect to the longitudinal axis A of the device.

Once the suction foot portion 8 has had its target plane positioned on the surface of the desired tissue or organ, such as the left ventricle of the heart, suction may be applied to the suction foot portion 8 by use of a syringe attached to vacuum port 12. This causes the suction foot portion 8 be firmly attached to the target site. With the suction foot portion 8 firmly in place, the lead may be fixed by turning knob 10 in order to cause the corkscrew-shaped lead terminal end 5a to be inserted into the tissue. With the lead 5 firmly in place, the hollow lead guide portion 2 is withdrawn toward the proximal end 6a of the elongated body portion 6. This causes the disk-shaped optional sleeve 4a to separate from the lead guide head 4, leaving the sleeve 4a on the tissue surface while the lead guide head 4 also separates from the suction foot portion 8. This allows the balance of the lead 5 to be deployed from within the hollow lead guide 2 as it recedes from the target site while being maintained within the elongated body portion 6.

From this point, the balance of the surgical operation and energizes of the pacing lead made be completed in accordance with methods and apparatus known and used in the art.

It will be appreciated that the mechanical arrangements in the device and the logical order of the steps in the described methods are used for purposes of illustration only, and that the steps may be varied where not otherwise inconsistent with the purpose and result obtained in the practice of the invention.

The invention may be embodied in other specific forms without departing from the spirit or essential characteristics thereof. The foregoing embodiments are therefore to be considered in all respects illustrative rather than limiting on the invention described herein. The scope of the invention is thus indicated by the appended claims rather than by the foregoing description, and all changes that come within the meaning and range of equivalency of the claims are intended to be embraced therein.

The present invention may be used in accordance with other methods and devices relating to lead and conduit placement, such as those described in the following references that are hereby incorporated herein by reference:

REFERENCES

Patent or Patent

Application Number

US 2004/0153098
U.S. Pat. No. 7,526,342
US 2003/0187461
US 2010/0312256
U.S. Pat. No. 7,544,197
U.S. Pat. No. 7,890,192
U.S. Pat. No. 7,930,040
US 2005/0004644
U.S. Pat. No. 6,132,456
U.S. Pat. No. 5,902,331
US 2004/0215139
U.S. Pat. No. 6,868,291
U.S. Pat. No. 5,882,333
U.S. Pat. No. 5,203,772
U.S. Pat. No. 6,697,677
US 2006/0009827
US 2009/0182347
US 2009/0198251
WO 2008058265
WO 2004058326
WO 9906104
EP 452278
U.S. Pat. No. 5,139,033
U.S. Pat. No. 4,146,037
U.S. Pat. No. 4,972,847
U.S. Pat. No. 5,342,413
U.S. Pat. No. 7,270,669
US 2006/0161238
U.S. Pat. No. 4,271,846
U.S. Pat. No. 5,972,013
US 2003/0187461
US 2010/0312256
U.S. Pat. No. 7,544,197
U.S. Pat. No. 7,890,192
U.S. Pat. No. 7,930,040
US 2005/0004644
U.S. Pat. No. 6,132,456
U.S. Pat. No. 5,902,331
US 2004/0215139
U.S. Pat. No. 6,868,291
U.S. Pat. No. 5,882,333
U.S. Pat. No. 5,203,772
U.S. Pat. No. 6,697,677
US 2006/0009827
US 2009/0182347
US 2009/0198251
WO 2008058265
WO 2004058326
WO 9906104
EP 452278
U.S. Pat. No. 5,139,033
U.S. Pat. No. 4,146,037
U.S. Pat. No. 4,972,847
U.S. Pat. No. 5,342,413
U.S. Pat. No. 7,270,669
US 2006/0161238
U.S. Pat. No. 4,271,846

What is claimed is:

1. A device adapted for the thoracoscopic placement of a lead at a target site on an epicardial surface of a heart, the device comprising:
   (a) a hollow lead guide;
   (b) a lead extending through said hollow lead guide, said lead having a lead distal end portion;
   (c) an elongated body having a longitudinal axis, a proximal end portion and a distal end portion, and having a proximal inlet and a distal lead outlet, said elongated body comprising (1) a lead receiving passageway for receiving and conducting said lead distal end to said distal lead outlet, and (2) a lumen adapted to provide suction to said distal end portion;
   (d) a suction foot portion releasably attached to said lead distal end portion, and being in fluid communication with said lumen, said suction foot portion swivelably attached to said distal end portion such that said suction foot portion may be swiveled with respect to said longitudinal axis, and;
   said lead adapted to releasably engage said suction foot portion such that such engagement is of sufficient strength to maintain the position of said lead distal end portion as it engages said epicardial surface of a heart, and sufficiently releasable such that said lead may be released from said suction foot portion once said lead is attached to said epicardial surface of a heart; and
   (e) an actuator extending from said proximal end portion to said distal end portion and adapted to tilt said suction foot portion about a first axis with respect to said longitudinal axis; and
   wherein said hollow lead guide is adapted to tilt said suction foot portion about a second axis with respect to said longitudinal axis.

2. The device of claim 1 wherein said elongated body has a handle portion extending laterally therefrom.

3. The device of claim 1 wherein said hollow lead guide comprises a lead guide distal end, and is connected to a lead guide head at said lead guide distal end, and additionally comprising a flexible member connecting said lead guide head to said lead guide distal end.

4. The device of claim 3 wherein flexible member is a spring.

5. The device of claim 3 wherein said flexible member is a spring and wherein, upon movement of said hollow lead guide within said elongated body, said suction foot portion may be tilted about a second of said axes.

6. The device of claim 1 wherein said hollow lead guide comprises a lead guide distal end, and is connected to a lead guide head at said lead guide distal end, and additionally comprising a knob so as to permit said hollow lead guide to be rotated within said elongated body by hand, so as to rotate said lead guide head.

7. The device of claim 1 wherein said suction foot portion has an engagement aperture aligned with said hollow lead guide, and wherein said lead guide head is adapted to releasably engage said engagement aperture.

8. The device of claim 1 wherein said suction foot portion has an arcuate footprint shape and comprises a plurality of air channels in fluid contact with said lumen, so as to be capable of providing suction to said suction foot portion.

9. The device of claim 8 wherein said suction foot portion defines an engagement aperture aligned with said hollow lead guide, and wherein said lead guide head is adapted to releasably engage said engagement aperture.

10. The device of claim 1 wherein said hollow lead guide comprises a lead guide distal end, and is connected to a lead guide head at said lead guide distal end, and wherein said lead distal end is held by said lead guide head so as to extend from the distal side of said lead guide head.

11. The device of claim 10, additionally comprising an interferant release collar attached to said lead distal end portion and disposed on the distal side of said suction foot portion, said interferant release collar being larger than said aperture.

12. The device of claim 1 wherein said actuator comprises a flexible member connecting said suction foot portion to said elongated body.

13. The device of claim 12 wherein flexible member is a spring.

14. The device of claim 1 wherein said actuator is attached to a knob portion disposed on said proximal end portion, said knob adapted to move said actuator within said elongated body so as to tilt said suction foot about a first of said axes.

15. The device of claim 1 wherein said actuator comprises a wire attached to a knob portion disposed on said proximal end portion, said knob adapted to move said actuator within said elongated body so as to tilt said suction foot about a first of said axes.

16. The device of claim 1, additionally comprising a source of vacuum suction in fluid communication with said lumen.

17. The device of claim 16, wherein said source of vacuum suction in fluid communication with said lumen is selected from the group consisting of a hand pump, or a syringe attached to said elongated body, or a motorized pump supplying vacuum suction to said lumen.

18. The device of claim 1, additionally comprising a test lead extending from said lead guide head and through said elongated body.

* * * * *